United States Patent
King et al.

(10) Patent No.: US 7,291,451 B2
(45) Date of Patent: Nov. 6, 2007

(54) MODULATION OF PERICYTE PROLIFERATION

(75) Inventors: George L. King, Boston, MA (US); Susan Abrahamson, Berkeley, CA (US); Michael Pugsley, Pleasant Hill, CA (US)

(73) Assignee: XOMA Technology Ltd., Berkeley, CA (US)

( * ) Notice: Subject to any disclaimer, the term of this patent is extended or adjusted under 35 U.S.C. 154(b) by 250 days.

(21) Appl. No.: 10/993,142

(22) Filed: Nov. 19, 2004

(65) Prior Publication Data

US 2005/0153889 A1   Jul. 14, 2005

Related U.S. Application Data

(63) Continuation of application No. 10/006,557, filed on Dec. 3, 2001, now abandoned.

(60) Provisional application No. 60/250,542, filed on Dec. 1, 2000.

(51) Int. Cl.
*C12Q 1/00* (2006.01)
*G01N 33/53* (2006.01)
*C12N 5/00* (2006.01)
*A61K 38/00* (2006.01)

(52) U.S. Cl. .......................... 435/4; 435/7.21; 435/7.9; 435/375; 435/383; 530/300; 530/350

(58) Field of Classification Search ................ 435/375, 435/383; 530/300, 350
See application file for complete search history.

(56) References Cited

U.S. PATENT DOCUMENTS

| | | | |
|---|---|---|---|
| 5,198,541 A | 3/1993 | Elsbach et al. | |
| 5,348,942 A | 9/1994 | Little et al. | |
| 5,420,019 A | 5/1995 | Theofan et al. | |
| 5,447,913 A | 9/1995 | Ammons et al. | |
| 5,494,896 A | 2/1996 | Hansbrough | |
| 5,523,288 A | 6/1996 | Cohen et al. | |
| 5,578,568 A | 11/1996 | Ammons et al. | |
| 5,578,572 A | 11/1996 | Horwitz et al. | |
| 5,627,153 A | 5/1997 | Little et al. | |
| 5,639,727 A | 6/1997 | Little | |
| 5,641,874 A | 6/1997 | Elsbach et al. | |
| 5,643,570 A | 7/1997 | Theofan et al. | |
| 5,643,875 A | 7/1997 | Friedmann et al. | |
| 5,646,114 A | 7/1997 | Lambert, Jr. | |
| 5,652,332 A | 7/1997 | Little | |
| 5,674,834 A | 10/1997 | Theofan et al. | |
| 5,703,038 A | 12/1997 | Ammons et al. | |
| 5,733,872 A | 3/1998 | Little | |
| 5,741,779 A | 4/1998 | White et al. | |
| 5,753,620 A | 5/1998 | Friedmann et al. | |
| 5,756,464 A | 5/1998 | Scannon et al. | |
| 5,763,567 A | 6/1998 | Little | |
| 5,783,561 A | 7/1998 | Horwitz et al. | |
| 5,807,818 A | 9/1998 | Little | |
| 5,827,816 A | 10/1998 | Theofan et al. | |
| 5,837,678 A | 11/1998 | Little | |
| 5,851,802 A | 12/1998 | Better | |
| 5,854,214 A | 12/1998 | Little | |
| 5,856,302 A | 1/1999 | Ammons et al. | |
| 5,856,438 A | 1/1999 | Little | |
| 5,858,974 A | 1/1999 | Little et al. | |
| 5,888,973 A | 3/1999 | Lambert, Jr. | |
| 5,888,977 A | 3/1999 | Giroir et al. | |
| 5,935,930 A | 8/1999 | White et al. | |
| 5,945,399 A | 8/1999 | Scannon et al. | |
| 5,948,408 A | 9/1999 | Elsbach et al. | |
| 5,952,302 A | 9/1999 | Friedmann et al. | |
| 5,980,897 A | 11/1999 | Elsbach et al. | |
| 5,990,086 A | 11/1999 | Giroir et al. | |
| 6,013,629 A | 1/2000 | Lambert, Jr. | |
| 6,013,631 A | 1/2000 | Horwitz et al. | |
| 6,376,211 B1 * | 4/2002 | Little et al. | ................... 435/21 |

FOREIGN PATENT DOCUMENTS

| | | |
|---|---|---|
| WO | WO 89/01486 | 2/1989 |
| WO | WO 94/20128 | 9/1994 |
| WO | WO 95/08344 | 3/1995 |
| WO | WO 95/19179 | 7/1995 |
| WO | WO 95/19180 | 7/1995 |
| WO | WO 96/01647 | 1/1996 |
| WO | WO 97/04008 | 2/1997 |
| WO | WO 97/42966 | 11/1997 |
| WO | WO 98/06415 | 2/1998 |
| WO | WO 00/43028 | 7/2000 |
| WO | WO 01/00655 | 4/2001 |

OTHER PUBLICATIONS

Doherty et al., "Gene Expression during Vascular Pericyte Differentiation," *Critical Review in Eukaryotic Gene Expression*, 9:1-17 (1999).

Elsback et al., "Separation and Purification of a Potent Bactericidal/Permeability-increasing Protein and a Closely Associated Phospholipase $A_2$ from Rabbit Polymorphonuclear Leukocytes," *The Journal of Biological Chemistry*, 254:11000-11009 (1979).

Elsbach et al., "Oxygen-Independent Antimicrobial Systems of Phagocytes," Inflammation: *Basic Principles and Clinical Correlates*, 603-636 (1992).

(Continued)

*Primary Examiner*—Michail Belyavskyi
(74) *Attorney, Agent, or Firm*—Anne Dollard; Janet M. McNicholas; John M. Polo

(57) ABSTRACT

Methods and materials for modulating pericyte and epithelial cell proliferation relating to BPI protein products or inhibitors thereof are provided.

2 Claims, 2 Drawing Sheets

OTHER PUBLICATIONS

Hu et al., "The effect of heparin on the maemodynamic and structural response in the rat to acute and chronic hypoxia," *Br. J. Exp. Path.*, 70:113-124 (1989).

Khoury et al., "Effects of Endotoxin on Lung Pericytes in Vitro," *Microvascular Research*, 56:71-84 (1998).

Khoury et al., "Heparin-Like Molecules Inhibit Pulmonary Vascular Pericyte Proliferation in vitro," *Am. J. Physiol. Lung Cell. Mol. Physiol.*, 279:L252-L261 (2000).

Ooi et al., "Endotoxin-neutralizing Properties of the 25 dK N-Terminal Fragment and a Newly Isolated 30 kD C-Terminal Fragment of the 55-60 kD Bactericidal/Permeability-increasing Protein of Human Nuetrophils," *J. Exp. Med.*, 174:649-655 (1991).

Rauniyar et al., "Compounds Derived from Human Bactericidal/Permeability Increasing Protein Suppress VEGF-Induced Retinal Endothelial Cell Growth and Hypoxia-Induced Retinal Neovascularization while Enhancing Retinal Pericyte Growth," *Investigative Ophthalmology & Visual Science*, 42:S243 (2001).

Rhodin et al., "Capillary growth in the mesentery of normal young rats. Intravital video and electron microscope analyses," *J. Submicrosc. Cytol. Pathol.*, 21:1-34 (1989).

Sims, "Experimental Biology 2000 Symposium on Capillaries: How their structure and function can alter to meet tissue demands," *Clinical and Experimental Pharmacology and Physiology*, 27:842-846 (2000).

Weiss et al., "Cellular and Subcellular Localization of the Bactericidal/Permeability-Increasing Protein of Neutrophils," *Blood*, 69:652-659 (1987).

\* cited by examiner

SEQUENCE LISTING

<160> NUMBER OF SEQ ID NOS: 15

<210> SEQ ID NO 1
<211> LENGTH: 1813
<212> TYPE: DNA
<213> ORGANISM: Homo sapiens
<220> FEATURE:
<221> NAME/KEY: CDS
<222> LOCATION: (31)..(1491)
<223> OTHER INFORMATION:
<220> FEATURE:
<221> NAME/KEY: mat_peptide
<222> LOCATION: (124)..(1491)
<223> OTHER INFORMATION:
<220> FEATURE:
<221> NAME/KEY: misc_feature
<223> OTHER INFORMATION: rBPI

<400> SEQUENCE: 1

```
caggccttga ggttttggca gctctggagg atg aga gag aac atg gcc agg ggc          54
                                 Met Arg Glu Asn Met Ala Arg Gly
                                     -30              -25
cct tgc aac gcg ccg aga tgg gtg tcc ctg atg gtg ctc gtc gcc ata         102
Pro Cys Asn Ala Pro Arg Trp Val Ser Leu Met Val Leu Val Ala Ile
        -20                 -15                 -10
ggc acc gcc gtg aca gcg gcc gtc aac cct ggc gtc gtg gtc agg atc         150
Gly Thr Ala Val Thr Ala Ala Val Asn Pro Gly Val Val Val Arg Ile
            -5                  -1  1                   5
tcc cag aag ggc ctg gac tac gcc agc cag cag ggg acg gcc gct ctg         198
Ser Gln Lys Gly Leu Asp Tyr Ala Ser Gln Gln Gly Thr Ala Ala Leu
10                  15                  20                  25
cag aag gag ctg aag agg atc aag att cct gac tac tca gac agc ttt         246
Gln Lys Glu Leu Lys Arg Ile Lys Ile Pro Asp Tyr Ser Asp Ser Phe
                30                  35                  40
aag atc aag cat ctt ggg aag ggg cat tat agc ttc tac agc atg gac         294
Lys Ile Lys His Leu Gly Lys Gly His Tyr Ser Phe Tyr Ser Met Asp
            45                  50                  55
atc cgt gaa ttc cag ctt ccc agt tcc cag ata agc atg gtg ccc aat         342
Ile Arg Glu Phe Gln Leu Pro Ser Ser Gln Ile Ser Met Val Pro Asn
        60                  65                  70
gtg ggc ctt aag ttc tcc atc agc aac gcc aat atc aag atc agc ggg         390
Val Gly Leu Lys Phe Ser Ile Ser Asn Ala Asn Ile Lys Ile Ser Gly
75                  80                  85
aaa tgg aag gca caa aag aga ttc tta aaa atg agc ggc aat ttt gac         438
Lys Trp Lys Ala Gln Lys Arg Phe Leu Lys Met Ser Gly Asn Phe Asp
90                  95                  100                 105
ctg agc ata gaa ggc atg tcc att tcg gct gat ctg aag ctg ggc agt         486
Leu Ser Ile Glu Gly Met Ser Ile Ser Ala Asp Leu Lys Leu Gly Ser
                110                 115                 120
aac ccc acg tca ggc aag ccc acc atc acc tgc tcc agc tgc agc agc         534
Asn Pro Thr Ser Gly Lys Pro Thr Ile Thr Cys Ser Ser Cys Ser Ser
            125                 130                 135
cac atc aac agt gtc cac gtg cac atc tca aag agc aaa gtc ggg tgg         582
His Ile Asn Ser Val His Val His Ile Ser Lys Ser Lys Val Gly Trp
        140                 145                 150
ctg atc caa ctc ttc cac aaa aaa att gag tct gcg ctt cga aac aag         630
Leu Ile Gln Leu Phe His Lys Lys Ile Glu Ser Ala Leu Arg Asn Lys
    155                 160                 165
atg aac agc cag gtc tgc gag aaa gtg acc aat tct gta tcc tcc aag         678
Met Asn Ser Gln Val Cys Glu Lys Val Thr Asn Ser Val Ser Ser Lys
170                 175                 180                 185
ctg caa cct tat ttc cag act ctg cca gta atg acc aaa ata gat tct         726
Leu Gln Pro Tyr Phe Gln Thr Leu Pro Val Met Thr Lys Ile Asp Ser
                190                 195                 200
gtg gct gga atc aac tat ggt ctg gtg gca cct cca gca acc acg gct         774
Val Ala Gly Ile Asn Tyr Gly Leu Val Ala Pro Pro Ala Thr Thr Ala
            205                 210                 215
gag acc ctg gat gta cag atg aag ggg gag ttt tac agt gag aac cac         822
Glu Thr Leu Asp Val Gln Met Lys Gly Glu Phe Tyr Ser Glu Asn His
        220                 225                 230
cac aat cca cct ccc ttt gct cca cca gtg atg gag ttt ccc gct gcc         870
```

```
                                                                      -continued
His Asn Pro Pro Pro Phe Ala Pro Pro Val Met Glu Phe Pro Ala Ala
    235                 240                 245
cat gac cgc atg gta tac ctg ggc ctc tca gac tac ttc ttc aac aca        918
His Asp Arg Met Val Tyr Leu Gly Leu Ser Asp Tyr Phe Phe Asn Thr
250                 255                 260                 265
gcc ggg ctt gta tac caa gag gct ggg gtc ttg aag atg acc ctt aga        966
Ala Gly Leu Val Tyr Gln Glu Ala Gly Val Leu Lys Met Thr Leu Arg
                270                 275                 280
gat gac atg att cca aag gag tcc aaa ttt cga ctg aca acc aag ttc       1014
Asp Asp Met Ile Pro Lys Glu Ser Lys Phe Arg Leu Thr Thr Lys Phe
                    285                 290                 295
ttt gga acc ttc cta cct gag gtg gcc aag aag ttt ccc aac atg aag       1062
Phe Gly Thr Phe Leu Pro Glu Val Ala Lys Lys Phe Pro Asn Met Lys
                300                 305                 310
ata cag atc cat gtc tca gcc tcc acc ccg cca cac ctg tct gtg cag       1110
Ile Gln Ile His Val Ser Ala Ser Thr Pro Pro His Leu Ser Val Gln
    315                 320                 325
ccc acc ggc ctt acc ttc tac cct gcc gtg gat gtc cag gcc ttt gcc       1158
Pro Thr Gly Leu Thr Phe Tyr Pro Ala Val Asp Val Gln Ala Phe Ala
330                 335                 340                 345
gtc ctc ccc aac tcc tcc ctg gct tcc ctc ttc ctg att ggc atg cac       1206
Val Leu Pro Asn Ser Ser Leu Ala Ser Leu Phe Leu Ile Gly Met His
                350                 355                 360
aca act ggt tcc atg gag gtc agc gcc gag tcc aac agg ctt gtt gga       1254
Thr Thr Gly Ser Met Glu Val Ser Ala Glu Ser Asn Arg Leu Val Gly
                    365                 370                 375
gag ctc aag ctg gat agg ctg ctc ctg gaa ctg aag cac tca aat att       1302
Glu Leu Lys Leu Asp Arg Leu Leu Leu Glu Leu Lys His Ser Asn Ile
                380                 385                 390
ggc ccc ttc ccg gtt gaa ttg ctg cag gat atc atg aac tac att gta       1350
Gly Pro Phe Pro Val Glu Leu Leu Gln Asp Ile Met Asn Tyr Ile Val
    395                 400                 405
ccc att ctt gtg ctg ccc agg gtt aac gag aaa cta cag aaa ggc ttc       1398
Pro Ile Leu Val Leu Pro Arg Val Asn Glu Lys Leu Gln Lys Gly Phe
410                 415                 420                 425
cct ctc ccg acg ccg gcc aga gtc cag ctc tac aac gta gtg ctt cag       1446
Pro Leu Pro Thr Pro Ala Arg Val Gln Leu Tyr Asn Val Val Leu Gln
                430                 435                 440
cct cac cag aac ttc ctg ctg ttc ggt gca gac gtt gtc tat aaa           1491
Pro His Gln Asn Phe Leu Leu Phe Gly Ala Asp Val Val Tyr Lys
                    445                 450                 455
tgaaggcacc aggggtgccg ggggctgtca gccgcacctg ttcctgatgg gctgtgggc     1551
accggctgcc tttccccagg gaatcctctc cagatcttaa ccaagagccc cttgcaaact   1611
tcttcgactc agattcagaa atgatctaaa acgaggaaaa cattattcat tggaaaagtg   1671
catggtgtgt attttaggga ttatgagctt ctttcaaggg ctaaggctgc agagatattt   1731
cctccaggaa tcgtgtttca attgtaacca agaaatttcc atttgtgctt catgaaaaaa   1791
aacttctggt ttttttcatg tg                                             1813

<210> SEQ ID NO 2
<211> LENGTH: 487
<212> TYPE: PRT
<213> ORGANISM: Homo sapiens
<220> FEATURE:
<221> NAME/KEY: misc_feature
<223> OTHER INFORMATION: rBPI

<400> SEQUENCE: 2

Met Arg Glu Asn Met Ala Arg Gly Pro Cys Asn Ala Pro Arg Trp Val
    -30                 -25                 -20
Ser Leu Met Val Leu Val Ala Ile Gly Thr Ala Val Thr Ala Ala Val
-15                 -10                  -5                  -1  1
Asn Pro Gly Val Val Val Arg Ile Ser Gln Lys Gly Leu Asp Tyr Ala
                5                   10                  15
Ser Gln Gln Gly Thr Ala Ala Leu Gln Lys Glu Leu Lys Arg Ile Lys
                    20                  25                  30
Ile Pro Asp Tyr Ser Asp Ser Phe Lys Ile Lys His Leu Gly Lys Gly
    35                  40                  45
His Tyr Ser Phe Tyr Ser Met Asp Ile Arg Glu Phe Gln Leu Pro Ser
50                  55                  60                  65
Ser Gln Ile Ser Met Val Pro Asn Val Gly Leu Lys Phe Ser Ile Ser
                70                  75                  80
Asn Ala Asn Ile Lys Ile Ser Gly Lys Trp Lys Ala Gln Lys Arg Phe
                    85                  90                  95
Leu Lys Met Ser Gly Asn Phe Asp Leu Ser Ile Glu Gly Met Ser Ile
    100                 105                 110
Ser Ala Asp Leu Lys Leu Gly Ser Asn Pro Thr Ser Gly Lys Pro Thr
115                 120                 125
```

-continued

```
Ile Thr Cys Ser Ser Cys Ser His Ile Asn Ser Val His Val His
130                 135                 140                 145
Ile Ser Lys Ser Lys Val Gly Trp Leu Ile Gln Leu Phe His Lys Lys
                150                 155                 160
Ile Glu Ser Ala Leu Arg Asn Lys Met Asn Ser Gln Val Cys Glu Lys
            165                 170                 175
Val Thr Asn Ser Val Ser Ser Lys Leu Gln Pro Tyr Phe Gln Thr Leu
        180                 185                 190
Pro Val Met Thr Lys Ile Asp Ser Val Ala Gly Ile Asn Tyr Gly Leu
    195                 200                 205
Val Ala Pro Pro Ala Thr Thr Ala Glu Thr Leu Asp Val Gln Met Lys
210                 215                 220                 225
Gly Glu Phe Tyr Ser Glu Asn His His Asn Pro Pro Phe Ala Pro
                230                 235                 240
Pro Val Met Glu Phe Pro Ala Ala His Asp Arg Met Val Tyr Leu Gly
            245                 250                 255
Leu Ser Asp Tyr Phe Phe Asn Thr Ala Gly Leu Val Tyr Gln Glu Ala
        260                 265                 270
Gly Val Leu Lys Met Thr Leu Arg Asp Asp Met Ile Pro Lys Glu Ser
    275                 280                 285
Lys Phe Arg Leu Thr Thr Lys Phe Phe Gly Thr Phe Leu Pro Glu Val
290                 295                 300                 305
Ala Lys Lys Phe Pro Asn Met Lys Ile Gln Ile His Val Ser Ala Ser
                310                 315                 320
Thr Pro Pro His Leu Ser Val Gln Pro Thr Gly Leu Thr Phe Tyr Pro
            325                 330                 335
Ala Val Asp Val Gln Ala Phe Ala Val Leu Pro Asn Ser Ser Leu Ala
        340                 345                 350
Ser Leu Phe Leu Ile Gly Met His Thr Thr Gly Ser Met Glu Val Ser
    355                 360                 365
Ala Glu Ser Asn Arg Leu Val Gly Glu Leu Lys Leu Asp Arg Leu Leu
370                 375                 380                 385
Leu Glu Leu Lys His Ser Asn Ile Gly Pro Phe Pro Val Glu Leu Leu
                390                 395                 400
Gln Asp Ile Met Asn Tyr Ile Val Pro Ile Leu Val Leu Pro Arg Val
            405                 410                 415
Asn Glu Lys Leu Gln Lys Gly Phe Pro Leu Pro Thr Pro Ala Arg Val
        420                 425                 430
Gln Leu Tyr Asn Val Val Leu Gln Pro His Gln Asn Phe Leu Leu Phe
    435                 440                 445
Gly Ala Asp Val Val Tyr Lys
450                 455

<210> SEQ ID NO 3
<211> LENGTH: 11
<212> TYPE: PRT
<213> ORGANISM: Homo sapiens
<220> FEATURE:
<221> NAME/KEY: MISC_FEATURE
<223> OTHER INFORMATION: XMP.679
<220> FEATURE:
<221> NAME/KEY: SITE
<222> LOCATION: (5)..(5)
<223> OTHER INFORMATION: /label=Substituted-Ala note=position 5 is 1-
      naph-ala
<220> FEATURE:
<221> NAME/KEY: SITE
<222> LOCATION: (9)..(9)
<223> OTHER INFORMATION: /label=Substituted-Ala note=position 9 is 1-
      naph-ala
<220> FEATURE:
<221> NAME/KEY: SITE
<222> LOCATION: (1)..(11)
<223> OTHER INFORMATION: /Label=D Amino Acids/note=Positions 1-11 are
      D-Amino Acids
<220> FEATURE:
<221> NAME/KEY: SITE
<222> LOCATION: (11)..(11)
<223> OTHER INFORMATION: AMIDATION /label=Amidation note=The C-terminus
      is Amidated

<400> SEQUENCE: 3

Lys Leu Phe Lys Ala Gln Ala Lys Ala Lys Gly
1               5                   10

<210> SEQ ID NO 4
```

```
<211> LENGTH: 11
<212> TYPE: PRT
<213> ORGANISM: Homo sapiens
<220> FEATURE:
<221> NAME/KEY: MISC_FEATURE
<223> OTHER INFORMATION: XMP.627
<220> FEATURE:
<221> NAME/KEY: SITE
<222> LOCATION: (5)..(5)
<223> OTHER INFORMATION: /label=Substituted Ala note=position 5 is
      1-naph-ala
<220> FEATURE:
<221> NAME/KEY: SITE
<222> LOCATION: (9)..(9)
<223> OTHER INFORMATION: /label=Substituted Ala note=position 9 is
      1- naph-ala
<220> FEATURE:
<221> NAME/KEY: SITE
<222> LOCATION: (1)..(11)
<223> OTHER INFORMATION: /Label=D Amino Acids/note=Positions 1-11 are
      D-amino acids
<220> FEATURE:
<221> NAME/KEY: SITE
<222> LOCATION: (11)..(11)
<223> OTHER INFORMATION: AMIDATION /label=Amidation note=The C-terminus
      is Amidated

<400> SEQUENCE: 4

Lys Leu Phe Arg Ala Gln Ala Lys Ala Lys Gly
1               5                   10

<210> SEQ ID NO 5
<211> LENGTH: 8
<212> TYPE: PRT
<213> ORGANISM: Homo sapiens
<220> FEATURE:
<221> NAME/KEY: MISC_FEATURE
<223> OTHER INFORMATION: XMP.664
<220> FEATURE:
<221> NAME/KEY: SITE
<222> LOCATION: (1)..(8)
<223> OTHER INFORMATION: Positions 1-8 are D-amino acids
<220> FEATURE:
<221> NAME/KEY: SITE
<222> LOCATION: (5)..(5)
<223> OTHER INFORMATION: Position 5 is substituted with 1- naph-ala
<220> FEATURE:
<221> NAME/KEY: SITE
<222> LOCATION: (1)..(1)
<223> OTHER INFORMATION: Position 1 is derivatized at the alpha-amino
      group with 4-biphenyl carbonyl
<220> FEATURE:
<221> NAME/KEY: SITE
<222> LOCATION: (8)..(8)
<223> OTHER INFORMATION: AMIDATION=The C-terminus is Amidated

<400> SEQUENCE: 5

Lys Leu Phe Arg Ala Gln Ala Lys
1               5

<210> SEQ ID NO 6
<211> LENGTH: 11
<212> TYPE: PRT
<213> ORGANISM: Homo sapiens
<220> FEATURE:
<221> NAME/KEY: MISC_FEATURE
<223> OTHER INFORMATION: XMP.728
<220> FEATURE:
<221> NAME/KEY: SITE
<222> LOCATION: (1)..(11)
<223> OTHER INFORMATION: Positions 1-11 are D-amino acids
<220> FEATURE:
<221> NAME/KEY: SITE
<222> LOCATION: (5)..(5)
<223> OTHER INFORMATION: Position 5 is substituted with 4-biphenyl-ala
```

```
<220> FEATURE:
<221> NAME/KEY: SITE
<222> LOCATION: (9)..(9)
<223> OTHER INFORMATION: Position 9 is substituted with 4-biphenyl-ala
<220> FEATURE:
<221> NAME/KEY: SITE
<222> LOCATION: (11)..(11)
<223> OTHER INFORMATION: AMIDATION=The C-terminus is Amidated

<400> SEQUENCE: 6

Lys Leu Phe Lys Ala Gln Ala Lys Ala Lys Gly
1               5                   10

<210> SEQ ID NO 7
<211> LENGTH: 5
<212> TYPE: PRT
<213> ORGANISM: Homo sapiens
<220> FEATURE:
<221> NAME/KEY: MISC_FEATURE
<223> OTHER INFORMATION: XMP.711
<220> FEATURE:
<221> NAME/KEY: SITE
<222> LOCATION: (1)..(1)
<223> OTHER INFORMATION: Position 1 is derivatized at the alpha-amino
      group with 4-biphenyl carbonyl
<220> FEATURE:
<221> NAME/KEY: SITE
<222> LOCATION: (3)..(3)
<223> OTHER INFORMATION: Position 3 is substituted with 4-biphenyl-ala
<220> FEATURE:
<221> NAME/KEY: SITE
<222> LOCATION: (1)..(2)
<223> OTHER INFORMATION: Positions 1-2 are D-amino acids
<220> FEATURE:
<221> NAME/KEY: SITE
<222> LOCATION: (3)..(3)
<223> OTHER INFORMATION: Position 3 is L-amino acid
<220> FEATURE:
<221> NAME/KEY: SITE
<222> LOCATION: (4)..(5)
<223> OTHER INFORMATION: Positions 4-5 are D-amino acids
<220> FEATURE:
<221> NAME/KEY: SITE
<222> LOCATION: (5)..(5)
<223> OTHER INFORMATION: AMIDATION=The C-terminus is Amidated

<400> SEQUENCE: 7

Lys Leu Ala Arg Lys
1               5

<210> SEQ ID NO 8
<211> LENGTH: 6
<212> TYPE: PRT
<213> ORGANISM: Homo sapiens
<220> FEATURE:
<221> NAME/KEY: MISC_FEATURE
<223> OTHER INFORMATION: XMP.852
<220> FEATURE:
<221> NAME/KEY: SITE
<222> LOCATION: (1)..(1)
<223> OTHER INFORMATION: Position 1 is derivatized at the alpha-amino
      group with 4-biphenyl carbonyl
<220> FEATURE:
<221> NAME/KEY: SITE
<222> LOCATION: (5)..(5)
<223> OTHER INFORMATION: Position 5 is substituted with 1- naph-ala
<220> FEATURE:
<221> NAME/KEY: SITE
<222> LOCATION: (1)..(6)
<223> OTHER INFORMATION: Positions 1-6 are D-amino acids
<220> FEATURE:
<221> NAME/KEY: SITE
<222> LOCATION: (6)..(6)
<223> OTHER INFORMATION: AMIDATION=The C-terminus is Amidated
```

```
<400> SEQUENCE: 8

Lys Leu Phe Arg Ala Gln
1               5

<210> SEQ ID NO 9
<211> LENGTH: 5
<212> TYPE: PRT
<213> ORGANISM: Homo sapiens
<220> FEATURE:
<221> NAME/KEY: MISC_FEATURE
<223> OTHER INFORMATION: XMP.861
<220> FEATURE:
<221> NAME/KEY: SITE
<222> LOCATION: (1)..(1)
<223> OTHER INFORMATION: Position 1 is derivatized at the alpha-amino
      group with 4-biphenyl carbonyl
<220> FEATURE:
<221> NAME/KEY: SITE
<222> LOCATION: (5)..(5)
<223> OTHER INFORMATION: Position 5 is substituted with 1- naph-ala
<220> FEATURE:
<221> NAME/KEY: SITE
<222> LOCATION: (1)..(5)
<223> OTHER INFORMATION: Positions 1-5 are D-amino acids
<220> FEATURE:
<221> NAME/KEY: SITE
<222> LOCATION: (5)..(5)
<223> OTHER INFORMATION: AMIDATION=The C-terminus is Amidated

<400> SEQUENCE: 9

Lys Leu Phe Arg Ala
1               5

<210> SEQ ID NO 10
<211> LENGTH: 6
<212> TYPE: PRT
<213> ORGANISM: Homo sapiens
<220> FEATURE:
<221> NAME/KEY: MISC_FEATURE
<223> OTHER INFORMATION: XMP.718
<220> FEATURE:
<221> NAME/KEY: SITE
<222> LOCATION: (1)..(1)
<223> OTHER INFORMATION: Position 1 is derivatized at the alpha-amino
      group with 4-biphenyl carbonyl
<220> FEATURE:
<221> NAME/KEY: SITE
<222> LOCATION: (6)..(6)
<223> OTHER INFORMATION: Position 6 is substituted with 1- naph-ala
<220> FEATURE:
<221> NAME/KEY: SITE
<222> LOCATION: (1)..(6)
<223> OTHER INFORMATION: Positions 1-6 are D-amino acids
<220> FEATURE:
<221> NAME/KEY: SITE
<222> LOCATION: (6)..(6)
<223> OTHER INFORMATION: AMIDATION=The C-terminus is Amidated
<220> FEATURE:
<221> NAME/KEY: SITE
<222> LOCATION: (3)..(3)
<223> OTHER INFORMATION: Position 3 is substituted with
      homophenylalanine

<400> SEQUENCE: 10

Lys Leu Phe Arg Lys Ala
1               5

<210> SEQ ID NO 11
<211> LENGTH: 10
<212> TYPE: PRT
<213> ORGANISM: Homo sapiens
<220> FEATURE:
<221> NAME/KEY: MISC_FEATURE
```

```
<223> OTHER INFORMATION: XMP.365
<220> FEATURE:
<221> NAME/KEY: SITE
<222> LOCATION: (1)..(10)
<223> OTHER INFORMATION: Positions 1-10 are D-amino acids
<220> FEATURE:
<221> NAME/KEY: SITE
<222> LOCATION: (10)..(10)
<223> OTHER INFORMATION: AMIDATION=The C-terminus is Amidated

<400> SEQUENCE: 11

Lys Trp Leu Ile Gln Leu Phe His Lys Lys
1               5                   10

<210> SEQ ID NO 12
<211> LENGTH: 9
<212> TYPE: PRT
<213> ORGANISM: Homo sapiens
<220> FEATURE:
<221> NAME/KEY: MISC_FEATURE
<223> OTHER INFORMATION: XMP.629
<220> FEATURE:
<221> NAME/KEY: SITE
<222> LOCATION: (5)..(5)
<223> OTHER INFORMATION: /label=Substituted-Ala note=position 5 is
      1- naph-ala
<220> FEATURE:
<221> NAME/KEY: SITE
<222> LOCATION: (9)..(9)
<223> OTHER INFORMATION: /label=Substituted-Ala note=position 9 is
      1- naph-ala
<220> FEATURE:
<221> NAME/KEY: SITE
<222> LOCATION: (1)..(9)
<223> OTHER INFORMATION: /Label=D Amino Acids/note=Positions 1-9 are
      D-amino acids
<220> FEATURE:
<221> NAME/KEY: SITE
<222> LOCATION: (9)..(9)
<223> OTHER INFORMATION: AMIDATION /label=Amidation note=The C-terminus
      is Amidated

<400> SEQUENCE: 12

Lys Leu Phe Arg Ala Gln Ala Lys Ala
1               5

<210> SEQ ID NO 13
<211> LENGTH: 10
<212> TYPE: PRT
<213> ORGANISM: Homo sapiens
<220> FEATURE:
<221> NAME/KEY: MISC_FEATURE
<223> OTHER INFORMATION: XMP.676
<220> FEATURE:
<221> NAME/KEY: SITE
<222> LOCATION: (2)..(2)
<223> OTHER INFORMATION: /label=Substituted-Ala note=position 2 is
      1- naph-ala
<220> FEATURE:
<221> NAME/KEY: SITE
<222> LOCATION: (8)..(8)
<223> OTHER INFORMATION: Position 8 is substituted with 2-thienyl-ala
<220> FEATURE:
<221> NAME/KEY: SITE
<222> LOCATION: (3)..(3)
<223> OTHER INFORMATION: Position 3 is substituted with norvaline
<220> FEATURE:
<221> NAME/KEY: SITE
<222> LOCATION: (6)..(6)
<223> OTHER INFORMATION: Position 6 is substituted with norvaline
<220> FEATURE:
<221> NAME/KEY: SITE
<222> LOCATION: (1)..(1)
<223> OTHER INFORMATION: Position 1 is D-amino acids
<220> FEATURE:
```

```
<221> NAME/KEY: SITE
<222> LOCATION: (9)..(10)
<223> OTHER INFORMATION: Positions 9-10 are D-amino acids
<220> FEATURE:
<221> NAME/KEY: SITE
<222> LOCATION: (2)..(8)
<223> OTHER INFORMATION: Positions 2-7 are L-amino acids

<400> SEQUENCE: 13

Lys Ala Val Ile Gln Val Val Ala Lys Lys
1               5                   10

<210> SEQ ID NO 14
<211> LENGTH: 8
<212> TYPE: PRT
<213> ORGANISM: Homo sapiens
<220> FEATURE:
<221> NAME/KEY: MISC_FEATURE
<223> OTHER INFORMATION: XMP.768
<220> FEATURE:
<221> NAME/KEY: SITE
<222> LOCATION: (1)..(8)
<223> OTHER INFORMATION: Positions 1-8 are D-amino acids
<220> FEATURE:
<221> NAME/KEY: SITE
<222> LOCATION: (5)..(5)
<223> OTHER INFORMATION: Position 5 is substituted with 4-biphenyl-ala
<220> FEATURE:
<221> NAME/KEY: SITE
<222> LOCATION: (1)..(1)
<223> OTHER INFORMATION: Position 1 is derivatized at the alpha-amino
      group with 4-biphenyl carbonyl
<220> FEATURE:
<221> NAME/KEY: SITE
<222> LOCATION: (8)..(8)
<223> OTHER INFORMATION: AMIDATION=The C-terminus is Amidated

<400> SEQUENCE: 14

Lys Leu Phe Arg Ala Gln Ala Lys
1               5

<210> SEQ ID NO 15
<211> LENGTH: 7
<212> TYPE: PRT
<213> ORGANISM: Homo sapiens
<220> FEATURE:
<221> NAME/KEY: MISC_FEATURE
<223> OTHER INFORMATION: XMP.851
<220> FEATURE:
<221> NAME/KEY: SITE
<222> LOCATION: (1)..(1)
<223> OTHER INFORMATION: Position 1 is derivatized at the alpha-amino
      group with 4-biphenyl carbonyl
<220> FEATURE:
<221> NAME/KEY: SITE
<222> LOCATION: (5)..(5)
<223> OTHER INFORMATION: Position 5 is substituted with 1- naph-ala
<220> FEATURE:
<221> NAME/KEY: SITE
<222> LOCATION: (1)..(7)
<223> OTHER INFORMATION: Positions 1-7 are D-amino acids
<220> FEATURE:
<221> NAME/KEY: SITE
<222> LOCATION: (7)..(7)
<223> OTHER INFORMATION: AMIDATION=The C-terminus is Amidated

<400> SEQUENCE: 15

Lys Leu Phe Arg Ala Gln Ala
1               5
```

MODULATION OF PERICYTE PROLIFERATION

This application is a continuation of U.S. application Ser. No. 10/006,557, filed on Dec. 3, 2001 (now abandoned) which claims benefit under 35 USC § 119(e) of U.S. provisional application Ser. No. 60/250,542, filed Dec. 1, 2000.

FIELD OF THE INVENTION

The present invention relates generally to novel therapeutic uses associated with the modulation of perivascular cell proliferation, including the use of BPI protein products, such as BPI-derived peptides, to enhance desirable pericyte proliferation. The present invention additionally relates to the use of inhibitors of BPI protein product-induced pericyte proliferation to inhibit deleterious pericyte proliferation.

BACKGROUND OF THE INVENTION

Microvascular perivascular cells ("pericytes") are defined by their location in vivo. The pericyte is a small ovoid shaped cell with many finger-like projections that parallel the capillary axis and partially surround an endothelial cell in a microvessel. Pericytes share a common basement membrane with the endothelial cell. They are elongated cells with the power of contraction that have been observed to have a variety of functional characteristics. Pericytes are widely distributed in the body and include mesangial cells (in the glomeruli of the kidney), Rouget cells, or mural cells (in the retina of the eye) [Hirschi & D'Amore, Cardiovasc Res 1996 October;32(4):687-98.]. Some of the pericyte functional characteristics observed in vivo and in vitro are that they regulate endothelial cell proliferation and differentiation, contract in a manner that either exacerbates or reduces endothelial cell junctional inflammatory leakage, synthesize and secrete a wide variety of vasoactive autoregulating agonists, and synthesize and release structural constituents of the basement membrane and extracellular matrix. [Shepro et al, FASEB J 1993 August;7(11):1031-8.] Pericytes have thus been implicated as playing a role in vasoconstriction as well as a role in capillary blood flow, in the formation of blood vessels, in the immune response (particularly in the central nervous system), and in the extrinsic coagulation pathway. In the kidney, the contractile properties of the mesangial cells and their synthesis of various factors and structural proteins help to regulate the function of the glomerulus. [Schlandoiff, 1987, FASEB J, 1:272-81.]

Pericytes have been suggested to be derived from undifferentiated mesenchymal cells that are recruited by primordial endothelium and then differentiate into pericytes in microvessels or smooth muscle cells in large vessels. Pericytes are also pluripotential progenitor cells and have been shown to differentiate into a variety of different cell types, including osteoblasts, chondrocytes, adipocytes, phagocytes, fibroblasts, and smooth muscle cells. [Sims, 2000, Clin. Exp. Ped. Physiol., 27:842-846.] Pericytes behave in a manner similar to osteoblasts in vitro, by forming a mineralized extracellular matrix and expressing a number of genes that are also expressed by osteoblasts. These cells also form a well-defined matrix of bone, cartilage, and fibrous tissue in vivo. [Doherty and Canfield, Crit Rev Eukaryot Gene Expr 9(1):1-17, 1999; Hirschi et al., Cardiovasc Res October;32(4):687-98, 1996.]

The pericyte has been implicated in a variety of pathologies including hypertension, atherosclerosis, complications of diabetes (both insulin-dependent and non-insulin-dependent), ovarian failure, multiple sclerosis, and tumor vascularization, as well as in normal aging.

Microvessels of spontaneously hypertensive rat brains have been shown to have a relatively higher number of pericytes and an increased ratio of pericytes to endothelial cells, numbers which increased following the onset of chronic hypertension in the rats. Pericyte contraction has been suggested to play a pivotal role in regulating the flow of blood within the brain microcirculation and perhaps in the etiology and inception of cerebrovascular disease. [Herman I M et al., Tissue Cell 1987;19(2):197-206.]

Pericytes have been identified in the inner intima, the outer media, and in the vasa vasora of the adventitia of large, medium and small human arteries. Recent studies have suggested that pericytes in the arteries may be responsible, at least in part, for mediating the vascular calcification commonly associated with atherosclerosis [Canfield et al., Z Kardiol 2000;89 Suppl 2:20-7.] Myxomatous tissue is a characteristic component of human coronary artery lesions and is found more often in restenotic lesions. This tissue represents a bulky accumulation of stellate-shaped cells of unknown histogenesis that are embedded in a loose stroma and may be involved in an immune response. Stellate cells represented a heterogenous population, sharing features of smooth muscle cells (SMCs), macrophages, as well as antigen-presenting dendritic cells. Some workers have concluded that stellate cells of myxomatous tissue represent a specific phenotype of mesenchymal cells, possibly pericytes, which is activated to express some markers of antigen-presenting cells. [Tjurmin et al., Arterioscler Thromb Vasc Biol 1999 January;19(1):83-97.]

In diabetes mellitus, pericytes may be involved in the development of angiopathy, retinopathy, polyneuropathy and nephropathy. Hyperglycemia may promote apoptosis and a loss of retinal capillary pericytes very early in the development of diabetic retinopathy [Ruggiero et al., 1997 Diabetes Metabolism 23:30-42; Hirschi & D'Amore, Cardiovasc Res 1996 October;32(4):687-98.]. It has been suggested that the sensitivity of retinal pericytes to degeneration in diabetes is due to their lesser ability to reproliferate (compared to, e.g., brain pericytes) in response to the metabolic injury of diabetes. [Wong et al. Diabetologia 1992 September;35(9):818-27.] There is also a difference in pericyte/endothelial cell ratio in the eye (one pericyte per endothelial cell) relative to other locations (neural 1:2, peripheral 1:20) [Speiser et al., 1968 Arch Ophthalmol 80:332-337; Orlidge and D'Amore, 1987, J Cell Biol. 105: 1455-1462; Sims et al., 1994 Anat Histol Embryol 23:232-238.]. Pericyte degeneration has also been observed to precede development of diabetic polyneuropathy and is associated with its severity. [Giannini et al., Ann Neurol 1995 April;37(4):498-504.] Pericytes have been implicated in the thickening of the glomerular capillary basement membrane observed in diabetic retinopathy. [Keys et al., 2000, FASEB J, 14:439-47.] During diabetes, mesangial cells show increased synthesis of various extracellular matrix (ECM) components. This increased synthesis of ECM is also accompanied by a decreased degradation of ECM. The major enzymes responsible for ECM degradation are a large group of enzymes collectively known as matrix metalloproteinases (MMPs). The mesangial cell and its pericellular matrix have a very active plasminogen cascade that can liberate plasmin locally to mediate matrix degradation both directly and indirectly, by activating the MMPs. Thus, it is possible that degeneration of mesangial cells mediates the decrease in ECM degradation seen in diabetic nephropathy [McLennan et al., *Cell Mol Biol (Noisy-le-grant)* 1999 February;45(1):123-35.]

Pericyte degeneration has also been observed in animal models of ovarian failure. Ovaries of adult female rats treated with testosterone propionate and anovulatory ovaries of middle-aged female rats both exhibited regression of vascular pericytes, T-cells and dendritic cells within the interstitial glands. It appears that the function of ovarian steroidogenic cells may be regulated by mesenchymal cells. [Bukovskya et al, *Steroids* 2000 April;65(4): 190-205.]

Changes in pericyte population have also been observed during aging. There appears to be regional variation in the age-associated changes in the brain microvasculature. In the frontal cortex and hippocampus, there appears to be an increase in basement membrane with increasing age, accompanied by increased pericyte mitochondrial size. In the frontal cortex, there is increased capillary lumen area but in the hippocampus there is decreased capillary lumen area in the hippocampus. [Hicks P, *Neurobiol Aging* 1983 Spring; 4(1):69-75.] The brains of aging rats have been found to have increased astrocyte and pericyte populations in the parietal cortex. [Peinado M A et al., *Microsc Res Tech* 1998 October;1:43(1):34-42.] At the ultrastructural level different anomalies of the cerebral microvasculature are encountered. These aberrations can either be attributed to degeneration processes or to the perivascular deposition of, e.g., collagen fibrils and other proteinaceous debris. [de Jong *Neurobiol. Aging* 1992 January-February; 13(1):73-81.]

Of interest is the disclosure in Hu et al., *Br. J Exp. Pathol.* 1989 April; 70(2): 113-24 that intermittent treatment of mice with heparin has been shown to reduce the right ventricular hypertrophy caused by hypoxia; administration of heparin reduced the proportion of arteries that became muscularized, particularly at the alveolar duct level where the pericyte is the precursor smooth muscle cell. See also Khoury et al., *Am. J Physiol. Lung Cell Mol. Physiol.*, 279:L252-L261, 2000, a report that heparin-like molecules inhibit pulmonary vascular pericyte proliferation in vitro.

Thus, there exists a need for an agents that modulate pericyte proliferation. In conditions where proliferation of pericytes is desirable, there is a need for agents that allow or enhance such proliferation to be enhanced. In conditions where proliferation of pericytes is deleterious, there is a need for agents that inhibit such proliferation.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254: 11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in U.S. Pat. No. 5,198,541 and FIG. 1 of Gray et al., *J. Biol. Chem.*, 264:9505 (1989), incorporated herein by reference. The Gray et al. nucleic acid and amino acid sequence are set out in SEQ ID NOS: 1 and 2 hereto. U.S. Pat. No. 5,198,541 discloses recombinant genes encoding and methods for expression of BPI proteins, including BPI holoprotein and fragments of BPI. Recombinant human BPI holoprotein has also been produced in which valine at position 151 is specified by GTG rather than GTC, residue 185 is glutamic acid (specified by GAG) rather than lysine (specified by AAG) and residue 417 is alanine (specified by GCT) rather than valine (specified by GTT). BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD possesses essentially all the anti-bacterial efficacy of the naturally-derived 55 kD human BPI holoprotein. [Ooi et al., *J. Bio. Chem.*, 262: 14891-14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. [Gazzano-Santoro et al., *Infect. Immun.* 60:4754-4761 (1992).] An N-terminal analog designated rBPI$_{21}$ (also referred to as rBPI(1-193)ala$^{132}$) has been described in U.S. Pat. No. 5,420,019.

The bactericidal effect of BPI was originally reported to be highly specific to gram-negative species, e.g., in Elsbach and Weiss, *Inflammation: Basic Principles and Clinical Correlates*, eds. Gallin et al., Chapter 30, Raven Press, Ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

BPI protein products have a wide variety of beneficial activities. BPI protein products are bactericidal for gram-negative bacteria, as described in U.S. Pat. Nos. 5,198,541, 5,641,874, 5,948,408, 5,980,897 and 5,523,288. International Publication No. WO 94/20130 proposes methods for treating subjects suffering from an infection (e.g. gastrointestinal) with a species from the gram-negative bacterial genus Helicobacter with BPI protein products. BPI protein products also enhance the effectiveness of antibiotic therapy in gram-negative bacterial infections, as described in U.S. Pat. Nos. 5,948,408, 5,980,897 and 5,523,288 and International Publication Nos. WO 89/01486 (PCT/US99/02700) and WO 95/08344 (PCT/US94/11255). BPI protein products are also bactericidal for gram-positive bacteria and mycoplasma, and enhance the effectiveness of antibiotics in gram-positive bacterial infections, as described in U.S. Pat. Nos. 5,578,572 and 5,783,561 and International Publication No. WO 95/19180 (PCT/US95/00656). BPI protein products exhibit antifungal activity, and enhance the activity of other antifungal agents, as described in U.S. Pat. No. 5,627, 153 and International Publication No. WO 95/19179 (PCT/US95/00498), and further as described for BPI-derived peptides in U.S. Pat. No. 5,858,974, which is in turn a continuation-in-part of U.S. application Ser. No. 08/504,841 and corresponding International Publication Nos. WO 96/08509 (PCT/US95/09262) and WO 97/04008 (PCT/US96/03845), as well as in U.S. Pat. Nos. 5,733,872, 5,763,567, 5,652,332, 5,856,438 and corresponding International Publication Nos. WO 94/20532 (PCT/US/94/02465) and WO 95/19372 (PCT/US94/10427). BPI protein products exhibit anti-protozoan activity, as described in U.S. Pat. Nos. 5,646,114 and 6,013,629 and International Publication No. WO 96/01647 (PCT/US95/08624). BPI protein products exhibit anti-chlamydial activity, as described in co-owned U.S. Pat. No. 5,888,973 and WO 98/06415 (PCT/US97/13810). Finally, BPI protein products exhibit anti-mycobacterial activity, as described in co-owned, co-pending U.S. application Ser. No. 08/626,646, which is in turn a continuation of U.S. application Ser. No. 08/285,803, which is in turn a continuation-in-part of U.S. application Ser. No. 08/031,145 and corresponding International Publication No. WO 94/20129 (PCT/US94/02463).

The effects of BPI protein products in humans with endotoxin in circulation, including effects on TNF, IL-6 and endotoxin are described in U.S. Pat. Nos. 5,643,875, 5,753,620 and 5,952,302 and corresponding International Publication No. WO 95/19784 (PCT/US95/01151).

BPI protein products are also useful for treatment of specific disease conditions, such as meningococcemia in humans (as described in U.S. Pat. Nos. 5,888,977 and 5,990,086 and International Publication No. WO97/42966 (PCT/US97/08016), hemorrhage due to trauma in humans, (as described in U.S. Pat. Nos. 5,756,464 and 5,945,399, U.S. application Ser. No. 08/862,785 and corresponding International Publication No. WO 97/44056 (PCT/US97/08941), burn injury (as described in U.S. Pat. No. 5,494,896 and corresponding International Publication No. WO 96/30037 (PCT/US96/02349)) ischemia/reperfusion injury (as described in U.S. Pat. No. 5,578,568), and depressed RES/liver resection (as described in co-owned, co-pending U.S. application Ser. No. 08/582,230 which is in turn a continuation of U.S. application Ser. No. 08/318,357, which is in turn a continuation-in-part of U.S. application Ser. No. 08/132,510, and corresponding International Publication No. WO 95/10297 (PCT/US94/11404).

BPI protein products also neutralize the anticoagulant activity of exogenous heparin, as described in U.S. Pat. No. 5,348,942, neutralize heparin in vitro as described in U.S. Pat. No. 5,854,214, and are useful for treating chronic inflammatory diseases such as rheumatoid and reactive arthritis, for inhibiting endothelial cell proliferation, and for inhibiting angiogenesis and for treating angiogenesis-associated disorders including malignant tumors, ocular retinopathy and endometriosis, as described in U.S. Pat. Nos. 5,639,727, 5,807,818 and 5,837,678 and International Publication No. WO 94/20128 (PCT/US94/02401).

BPI protein products are also useful in antithrombotic methods, as described in U.S. Pat. Nos. 5,741,779 and 5,935,930 and corresponding International Publication No. WO 97/42967 (PCT/US7/08017).

SUMMARY OF THE INVENTION

The present invention provides novel therapeutic methods of modulating proliferation of pericytes, including mural cells of the retina and mesangial cells of the kidney. In conditions where pericyte proliferation is desirable, the invention provides methods of using a therapeutically effective amount of a BPI protein product to enhance pericyte proliferation. Such conditions include complications of diabetes (both insulin-dependent and non-insulin-dependent), other diseases associated with the presence of autoantibodies to pericytes, age-related macular degeneration (ARMD), ovarian failure, multiple sclerosis, Alzheimer's disease, traumatic brain injury or other conditions involving perturbation of the blood-brain-barrier, partial seizures and placental development in pregnancy. In particular, sequelae of diabetes mellitus include diabetic retinopathy, diabetic polyneuropathy, diabetic nephropathy, skeletal muscle degeneration after pericyte degeneration, or other organ complications.

In conditions where pericyte proliferation is deleterious, the invention provides methods of inhibiting pericyte proliferation using therapeutically effective amounts of inhibitors capable of inhibiting the type of proliferation induced by BPI protein product, e.g., antibodies or other agents capable of binding to BPI protein product or otherwise inhibiting interaction with its receptor or ligand, or antagonists of the pericyte receptor that recognizes BPI protein products. Such conditions include hypertension, vascular disease, atherosclerosis, including formation of vascular calcifications and atherosclerotic plaques, restenosis, acute respiratory distress syndrome (ARDS), endometriosis or adenomyosis, and normal aging. In particular, sequelae of hypertension, atherosclerosis and other vascular diseases include cerebrovascular ischemia or stroke, coronary artery disease and myocardial ischemia or infarction, peripheral vascular disease, Raynaud's syndrome, early occlusion of peripheral arteries or vascular remodeling associated with pulmonary hypertension.

Uses of BPI protein products according to the invention are specifically contemplated in mammals, particularly humans, for prophylactic or therapeutic treatment of disease states or conditions mediated or exacerbated by pericyte proliferation or degeneration.

Studies suggest that undifferentiated mesenchymal cells or fibroblasts transform into capillary pericytes which in turn transform into vascular smooth muscle and other related cells such as adipocytes, osteoblasts and phagocytes [Rhodin & Fujita 1989 *Submicrosc Cytol Pathol* 21:1-34; Doherty & Canfield 1999 *Crit Rev Euk Gene Exp* 9(1):1-17]. Thus, further provided are methods for enhancing the production or formation of osteoblasts, chondrocytes, adipocytes, phagocytes, fibroblasts, and smooth muscle cells from pericytes and thus repairing or replacing damaged tissue, e.g. in wounds. In addition to enhancing proliferation of such cells per se, BPI protein products, including BPI-derived peptides, may be expected to enhance differentiation of pericytes into certain cell types, or to enhance proliferation of the finally differentiated cell types. Such methods are expected to be useful in a variety of conditions including enhancing wound healing, treatment of bone fractures or bone degenerative disorders.

Exemplary BPI protein products include recombinantly-produced N-terminal analogs or fragments of BPI, especially those having a molecular weight of approximately between 20 to 25 kD such as $rBPI_{21}$, $rBPI_{23}$, rBPI(10-193) C132A (also designated rBPI(10-193)ala$^{32}$), dimeric forms of these N-terminal polypeptides (e.g., $rBPI_{42}$ dimer), or BPI-derived peptides. Exemplary BPI-derived peptides include peptides derived from BPI domain II, such as XMP.679 ([SEQ ID NO: 3]), the structure and activity of which are described in co-owned U.S. Ser. No. 09/602,811 filed Jun. 23, 2000, which is a continuation-in-part of U.S. Ser. No. 09/344,219 filed Jun. 25, 1999, each incorporated herein by reference.

It is contemplated that the administration of a BPI protein product may be accompanied by the concurrent administration of other therapeutic agents, such as growth factors that enhance proliferation of pericytes or inhibitors of such growth factors, depending on the condition.

The invention also provides methods of screening for other BPI protein products that enhance pericyte proliferation. Such methods would comprise steps of, e.g., detecting or measuring growth or proliferation of pericytes in the presence and optionally the absence of a BPI protein product. Optionally the screening methods involve a further step of testing selected candidate compounds in animal models of pericyte proliferation wherein the proliferation results in desirable effects. The screening methods may also involve a further step of testing selected candidate compounds for ability to inhibit endothelial cell proliferation or angiogenesis (vasculogenesis). BPI protein products, including BPI-derived peptides, can be screened for proliferation-promoting activity using these methods. In addition, the rational design of molecules that function like pericyte proliferation-enhancing BPI protein products is contemplated. For example, peptides or other organic molecules may be synthesized that mimic the structure and function of BPI protein products with the desired pericyte proliferation-enhancing activity.

The invention also provides methods of screening for a candidate enhancer of pericyte proliferation including (a) measuring proliferation of pericytes in the presence and absence of a test compound, (b) measuring proliferation in the presence of the test compound and a BPI protein product (preferably at a concentration effective to enhance pericyte proliferation), and identifying the test compound as a candidate enhancer of pericyte proliferation when pericyte proliferation is increased in step (a) but not further increased in step (b), or when the increase in pericyte proliferation measured in step (a) is about the same as or less than the increase in pericyte proliferation measured in step (b).

The invention further provides methods of screening organic or inorganic compounds for the ability to inhibit proliferation induced by BPI protein products. Suitable standards for use in such screening assays include any BPI protein product that enhances pericyte proliferation, e.g., rBPI$_{21}$ or XMP.679. Such methods would comprise steps of, e.g., contacting pericytes with a BPI protein product and a candidate compound, and detecting or measuring growth or proliferation of the cells in the presence and absence of the test compound. A test compound is identified as a candidate inhibitor of BPI-induced proliferation when proliferation of the pericytes induced by the BPI protein product is reduced in the presence of the test compound. Optionally, as a control, the growth or proliferation of the pericytes is also measured in the presence and absence of the test compound alone (in the absence of BPI protein product). The screening methods may involve a further step of testing selected candidate compounds in animal models of pericyte proliferation wherein the proliferation results in deleterious effects. These methods according to the invention can be used for high throughput screening of libraries of molecules, such as inorganic or organic compounds (including bacterial, fungal, mammalian, insect or plant products, peptides, peptidomimetics and/or organomimetics).

Further provided are compounds identified by the screening methods described herein as well as methods of treatment using these compounds, to modulate (i.e., allow or enhance or inhibit) pericyte proliferation.

Yet another aspect of the invention provides methods for enhancing epithelial cell proliferation, particularly in the retina, by administering an effective amount of a BPI protein product, and methods for screening for compounds, either BPI protein products, BPI protein product mimetics, or small molecules, that allow or enhance epithelial cell proliferation, particularly in the retina (e.g. retinitis pigmentosa or choroidal neovascularisation seen in age-related macular degeneration [Campochiaro et al., *Molecular Vision,* 1999, 5:34 (1999)]), in wounds or bone fractures. Corresponding use of BPI protein products in preparation of a medicament for the treatment of diseases involving epithelial cell degeneration or diseases that would benefit from epithelial cell (particularly retinal epithelial cell) proliferation is also contemplated. In addition, this aspect of the invention includes corresponding methods of screening for other BPI protein products for the ability to enhance epithelial cell proliferation, particularly retinal epithelial cell proliferation, and methods of screening organic or inorganic compounds for the ability to inhibit epithelial cell proliferation induced by BPI protein products.

Numerous additional aspects and advantages of the invention will become apparent to those skilled in the art upon consideration of the following detailed description of the invention which describes presently preferred embodiments thereof.

DETAILED DESCRIPTION OF THE INVENTION

Figure 1A:
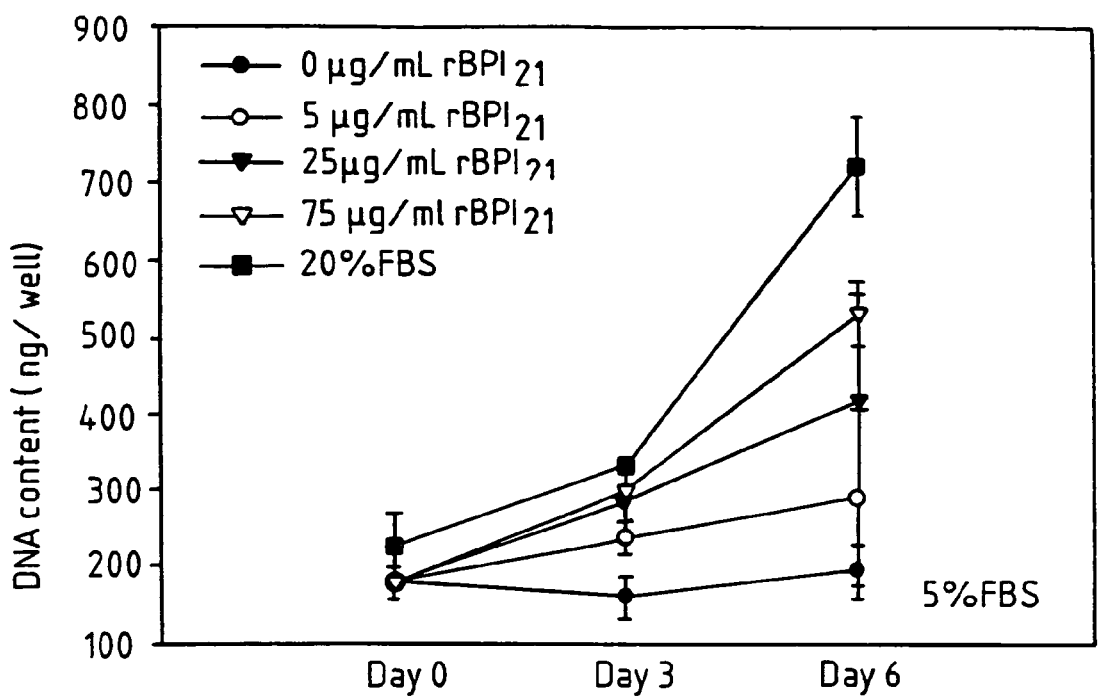
FIGS. 1A-1B display effects of BPI protein products on bovine retinal pericyte proliferation.

Pericytes are found throughout the body surrounding endothelial cells in microvessels, including in the skin, retina, cochlea (auditory apparatus), brain, heart, muscle, kidney, placenta, liver, lung, spleen and bone marrow include the mural cells of the retina, the mesangial cells of the kidney glomerulus, the Ito cells of the liver, and the reticular cells of the spleen and bone marrow. The present invention provides novel therapeutic uses and screening methods involving modulation of pericyte proliferation systemically or locally. The invention is based on the unexpected finding that BPI protein products, including rBPI$_{21}$ and BPI-derived peptides, stimulate proliferation of pericytes. In contrast to the anti-angiogenic, anti-inflammatory, anti-microbial and other properties of BPI protein products, which have been described in a number of different co-owned patents and applications, including those described hereinabove or below, the present invention with respect to use of BPI protein products is based on the modulation of pericyte-mediated effects.

The invention contemplates methods for treating disease states or conditions associated with, resulting from or exacerbated by pericyte degeneration, by administration of an amount of a BPI protein product effective to enhance pericyte proliferation. In this method, co-administration of other growth factors that enhance pericyte proliferation is also contemplated. Degeneration of pericytes is believed to be involved in the pathogenesis of complications of diabetes (both insulin-dependent and non-insulin-dependent), other diseases associated with the presence of autoantibodies to pericytes [Attawia et al., *Retina,* 1999; 19(5):390-400 report that diabetic subjects have been found to have autoantibodies to microvascular pericytes in their circulation], age-related macular degeneration (ARMD)) [Monaco & Wormington *Optim Vis Sci* 1990 July;67(7):532-7; Hope et al., *Br J Ophthalmol.* 1992 January;76(1):11-16], ovarian failure, multiple sclerosis [Verbeck et al., *J. Immunol.*, 154:5876-84 (1995)], Alzheimer's disease [Verbeek et al., 1997, *J. Neurochem*, 68:1135, Verbeek et al., 1999, *Cell. Mol. Biol.*, 45:37-46; Farkas et al., *Acta Neuropathol (Berl)* 2000 October;100(4):395-402], traumatic brain injury or other conditions involving perturbation of the blood-brain-barrier [Dore-Duffy et al., *Microvasc. Res.*, 2000, 60(1):55-69], partial seizures [Liwnicz et al., 1990 *Neurosurg*. 26(3):409-420], and placental development in pregnancy [Ohlsson et al., *Dev. Biol.* 1999:212(1):124-36; Challier et al., *Cell Mol. Biol.* 1999, 45(1):89-100]. Enhancing proliferation of pericytes or even merely ameliorating the degree of degeneration of pericytes thus may prevent or reduce onset and severity of these disorders and their sequelae. In particular, sequelae of diabetes mellitus include diabetic retinopathy, diabetic polyneuropathy, diabetic nephropathy, skeletal muscle degeneration after pericyte degeneration, or other organ complications.

Endotoxin is a potent pulmonary pericyte mitogen; in sepsis, pericytes may be involved in post-sepsis tissue remodeling. [Sims, 2000, *Clin. Exp. Ped. Physiol.*, 27:842; Khoury et al., *Microvasc. Res.*, 1998, 56:71-84.]

Pericyte degeneration is observed very early in diabetes mellitus, before any of the potential complications of diabetes mellitus are observed. Reversal of such degeneration via enhancement of pericyte proliferation is thus expected to be beneficial to subjects suffering from diabetes mellitus during the time period before onset or development of complications, even before the histologic or clinical changes of angiopathy or nephropathy have been observed. Early histological changes include thickened retinal cell basement membrane, pericyte degeneration, capillary microaneurysm, and arteriolar hyalinization. As disease progression occurs, increased vascular permeability and progressive retinal vessel closure results in clinical manifestations such as increasing vision loss and retinal necrosis. [Hammer et al., 1991 *Proc. Nat'l Acad. Sci. USA,* 88:11555.]

The invention also contemplates methods for treating disease states or conditions associated with, resulting from or exacerbated by pericyte proliferation by administration of an amount of a BPI inhibitor effective to reduce or eliminate pericyte proliferation. Proliferation of pericytes is believed to play a role in hypertension, vascular disease, atherosclerosis, including formation of vascular calcifications and atherosclerotic plaques, restenosis, acute respiratory distress syndrome (ARDS) [Kim et al., 1998, Hypertension, 31:511-515], endometriosis or adenomyosis [Mai et al., *Histopathology* 1997;30(5):430-42], and normal aging [Hicks et al., 1983, *Neurobiol. Aging* 4(1):69-75]. Reducing or even entirely preventing proliferation of pericytes thus may prevent or reduce onset or severity of these diseases, disorders associated with them, or their sequelae. In particular, sequelae of hypertension, atherosclerosis and other vascular diseases include cerebrovascular ischemia or stroke, coronary artery disease and myocardial ischemia or infarction, peripheral vascular disease, Raynaud's syndrome, early occlusion of peripheral arteries or vascular remodeling associated with pulmonary hypertension [Khoury et al., 2000, *Am. J. Physiol. Lung Cell. Mol. Physiol.,* 279(2):L252-L261.]

Further provided by the invention are methods for enhancing the production or formation or proliferation of osteoblasts, chondrocytes, adipocytes, phagocytes, fibroblasts, and smooth muscle cells from pericytes [Schor et al., 1995, *Clin. Orthoped. Rel. Res.,* 313:81-91; Sims, 2000, Clin. Exp. Ped. Physiol., 27:842-846] and thus repairing or replacing damaged tissue. Enhancing the formation or proliferation of osteoblasts or chondrocytes is expected to be beneficial in conditions associated with bone or cartilage loss or degeneration, referred to herein as a "bone degenerative disorder," including osteoporosis, osteonecrosis, osteomalacia, rickets, rheumatoid arthritis [Doherty et al., 1998, *J. Bone Min. Res.,* 13:828-838], osteoarthritis, bone fractures, bone grafts, surgical loss of bone, or tendon or ligament formation. Formation or proliferation of fibroblasts is expected to be beneficial in wound healing including burns, incisions, ulcers, skin grafting. Formation or proliferation of phagocytes is expected to be beneficial in situations involving exposure to infectious agents.

The term "treating" or "treatment" as used herein encompasses both prophylactic and therapeutic treatment, and may be accompanied by concurrent administration or co-administration of other therapeutic agents having a desired effect. Treatment of any subject is contemplated, especially mammalian subjects such as humans, but also including farm animals such as cows, sheep, pigs, horses, goats or poultry (e.g., chickens, turkeys, ducks or geese), companion animals such as dogs or cats, exotic and/or zoo animals, or laboratory animals including mice, rats, rabbits, guinea pigs, or hamsters.

"Concurrent administration," or "co-administration," as used herein includes administration of one or more agents, in conjunction, or in combination, together, or before or after each other. The agents may be administered by the same or by different routes. If administered via the same route, the agents may be given simultaneously or sequentially, as long as they are given in a manner sufficient to allow all agents to achieve effective concentrations at the site of action.

Therapeutic compositions may be administered systemically, locally into the appropriate area, or topically. Systemic routes of administration include oral, intravenous, intramuscular or subcutaneous injection (including into a depot for long-term release), intraocular or retrobulbar, intrathecal, intraperitoneal (e.g. by intraperitoneal lavage), intrapulmonary (using powdered drug, or an aerosolized or nebulized drug solution), or transdermal. In some instances, it is advantageous to administer the BPI protein product regionally or locally by selective catheterization of an involved vessel or by direct injection into the local area (e.g., into a depot for long-term release). It may also be advantageous to administer BPI protein product covalently or noncovalently linked to a targeting agent, e.g. an antibody specific for a tissue or cell type. Suitable dosages for systemic or local administration include doses ranging from 1 μg/kg to 100 mg/kg per day or doses ranging from 0.1 mg/kg to 20 mg/kg per day. The treatment may be continuous or by intermittent administration, at the same, reduced or increased dose per day for as long as determined by the treating physician.

Topical routes include administration in the form of salves, creams, jellies, ophthalmic drops or ointments (as described in co-owned, co-pending U.S. application Ser. No. 08/557,289 and 08/557,287, both filed Nov. 14, 1995), ear drops, suppositories, irrigation fluids (for, e.g., irrigation of wounds) or medicated shampoos. For example, for topical administration in drop form, about 10 to 200 μL of a therapeutic composition may be applied one or more times per day as determined by the treating physician.

Those skilled in the art can readily optimize effective dosages and administration regimens for therapeutic compositions as determined by good medical practice and the clinical condition of the individual subject.

As used herein, "BPI protein product" includes naturally or recombinantly produced BPI protein; natural, synthetic, or recombinant biologically active polypeptide fragments of BPI protein; biologically active polypeptide variants of BPI protein or fragments thereof, including hybrid fusion proteins or dimers; biologically active polypeptide analogs of BPI protein or fragments or variants thereof, including cysteine-substituted analogs; or BPI-derived peptides. The BPI protein products administered according to this invention may be generated and/or isolated by any means known in the art. U.S. Pat. Nos. 5,198,541 and 5,641,874, the disclosures of which are incorporated herein by reference, disclose recombinant genes encoding, and methods for expression of, BPI proteins including recombinant BPI holoprotein, referred to as rBPI and recombinant fragments of BPI. U.S. Pat. No. 5,439,807 and corresponding International Publication No. WO 93/23540 (PCT/US93/04752), which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein, including those described in U.S. Pat. Nos. 5,198,541 and 5,641,874. Non-limiting examples of such fragments include an N-terminal fragment of natural human BPI of approximately 25 kD, described in Ooi et al., *J. Exp. Med.,* 174:649 (1991), or the recombinant expression product of DNA encoding N-terminal amino acids from 1 to about 193 to 199 of natural human BPI, described in Gazzano-Santoro et al., *Infect. Immun.* 60:4754-4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra, with the exceptions noted for $rBPI_{23}$ and with the exception that residue 417 is alanine (specified by GCT) rather than valine (specified by GTT). Another fragment consisting of residues 10-193 of BPI has been described in U.S. Pat. No. 6,013,631, continuation-in-part U.S. application Ser. No. 09/336,402, filed Jun. 18, 1999, and corresponding International Publication No. WO 99/66044 (PCT/US99/13860), all of which are incorporated herein by reference. Other examples include dimeric forms of BPI fragments, as described in U.S. Pat. Nos. 5,447,913, 5,703,038, and 5,856,302 and corresponding International Publication No. WO 95/24209 (PCT/US95/03125), all of which are incorporated herein by reference.

Biologically active variants of BPI (BPI variants) include but are not limited to recombinant hybrid fusion proteins, comprising BPI holoprotein or biologically active fragment thereof and at least a portion of at least one other polypeptide, or dimeric forms of BPI variants. Examples of such hybrid fusion proteins and dimeric forms are described in U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof (e.g., a BPI—Ig fusion protein).

Biologically active analogs of BPI (BPI analogs) include but are not limited to BPI protein products wherein one or more amino acid residues have been replaced by a different amino acid. For example, U.S. Pat. Nos. 5,420,019, 5,674,834 and 5,827,816 and corresponding International Publication No. WO 94/18323 (PCT/US94/01235), all of which are incorporated herein by reference, discloses polypeptide analogs of BPI and BPI fragments wherein a cysteine residue is replaced by a different amino acid. A stable BPI protein product described by this application is the expression product of DNA encoding from amino acid I to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Production of this N-terminal analog of BPI, $rBPI_{21}$, has been described in Horwitz et al., *Protein Expression Purification,* 8:28-40 (1996). Similarly, an analog consisting of residues 10-193 of BPI in which the cysteine at position 132 is replaced with an alanine (designated "rBPI(10-193) C132A" or "rBPI(10-193)ala$^{132}$") has been described in U.S. Pat. No. 6,013,631, continuation-in-part U.S. application Ser. No. 09/336,402, filed Jun. 18, 1999, and corresponding International Publication No. WO 99/66044 (PCT/US99/13860), all of which are incorporated herein by reference. Other examples include dimeric forms of BPI analogs; e.g. U.S. Pat. Nos. 5,447,913, 5,703,038, and 5,856,302 and corresponding International Publication No. WO 95/24209 (PCT/US95/03125), all of which are incorporated herein by reference.

Other BPI protein products useful according to the methods of the invention are peptides derived from or based on BPI produced by synthetic or recombinant means (BPI-derived peptides), such as those described in International Publication No. WO 97/04008 (PCT/US96/03845), which corresponds to U.S. application Ser. No. 08/621,259 filed Mar. 21, 1996, and International Publication No. WO 96/08509 (PCT/US95/09262), which corresponds to U.S. Pat. No. 5,858,974, and International Publication No. WO 95/19372 (PCT/US94/10427), which corresponds to U.S. Pat. Nos. 5,652,332 and 5,856,438, and International Publication No. WO94/20532 (PCT/US94/02465), which corresponds to U.S. Pat. No. 5,763,567 which is a continuation of U.S. Pat. No. 5,733,872, which is a continuation-in-part of U.S. application Ser. No. 08/183,222, filed Jan. 14, 1994, which is a continuation-in-part of U.S. application Ser. No. 08/093,202 filed Jul. 15, 1993 (corresponding to International Publication No. WO 94/20128 (PCT/US94/02401)), which is a continuation-in-part of U.S. Pat. No. 5,348,942, as well as International Application No. PCT/US97/05287, which corresponds to U.S. Pat. No. 5,851,802, the disclosures of all of which are incorporated herein by reference. Methods of recombinant peptide production are described in U.S. Pat. No. 5,851,802 and International Publication No. WO 97/35009 (PCT/US97/05287), the disclosures of which are incorporated herein by reference.

Exemplary BPI protein products include recombinantly-produced N-terminal analogs or fragments of BPI, especially those having a molecular weight of approximately between 20 to 25 kD such as $rBPI_{21}$, $rBPI_{23}$, rBPI(10-193) C132A, (rBPI(10-193)ala$^{132}$), dimeric forms of these N-terminal polypeptides (e.g., $rBPI_{42}$ dimer), or BPI-derived peptides. Exemplary BPI-derived peptides include peptides derived from domain II of BPI, such as XMP.679 [the structure and activity of which are described in co-owned U.S. Ser. No. 09/602,811 filed Jun. 23, 2000, which is a continuation-in-part of U.S. Ser. No. 09/344,219 filed Jun. 25, 1999, each incorporated herein by reference].

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants or other therapeutic agents. A stable pharmaceutical composition containing BPI protein products (e.g., $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., $rBPI_{21}$) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. Nos. 5,488,034, 5,696,090 and 5,955,427 and corresponding International Publication No. WO 94/17819 (PCT/US94/01239), the disclosures of all of which are incorporated herein by reference. As described in U.S. Pat. No. 5,912,228 and corresponding International Publication No. WO96/21436 (PCT/US96/01095), all of which are incorporated herein by reference, other poloxamer formulations of BPI protein products with enhanced activity may be utilized, optionally with EDTA.

Growth factors contemplated according to the methods of the present invention include endothelin-I or platelet-derived growth factor-β (PDGF-β), both of which have been suggested to induce or enhance pericyte proliferation [Yamagishi et al., *Biochem Biophys Res Commun* 1993 Mar. 31;191(3):840-6; Hellstrom et al., *Development* 1999 June; 126(14):3047-55], PDGF (or PDGF A chain or AA or AB or B chain or BB) and transforming growth factor-beta (TGF-β) (or TGF-α, -β1, -β1.2, -β2, -β3, -β5, or latent TGF-β1), vascular permeability factor/vascular endothelial growth factor (VPF/VEGF), acidic fibroblast growth factor (aFGF), basic fibroblast growth factor (bFGF), FGF-4, -5, -6, -7, -8, -8b, -8c, -9, -10, endothelial cell growth factor (ECGF) or β-ECGF, as well as known angiopoietins (e.g., Ang-1, Ang-2, Ang-4, or Ang-Y), angiogenin, bone morphogenic proteins (BMPs, e.g., BMP-1, -2, -3, -4, -5, -6, -7, -8, -9, -10, -11, -12, -13, -14 or -15), bone morphogenic protein receptor 1A or IB, brain derived neurotrophic factor (BDNF), ciliary neutrophic factor (CNF), ciliary neutrophic factor receptor α, cytokine-induced neutrophil chemotactic factor 1, cytokine-induced neutrophil, chemotactic factor 2 α, cytokine-induced neutrophil chemotactic factor 2 β, epidermal growth factor, epithelial-derived neutrophil attractant, glial cell line-derived neutrophic factor receptor α 1, glial cell line-derived neutrophic factor receptor α 2, growth related protein, growth related protein a, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor receptor α, platelet derived growth factor receptor β, pre-B cell growth stimulating factor, stem cell factor, stem cell factor receptor, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

A "BPI inhibitor" as used herein includes any agent (except for heparin and heparin-like molecules [Khoury et al., *Am. J. Physiol. Lung Cell Mol. Physiol.*, 279:L252-L261, 2000; Hu et al., *Br. J Exp. Pathol.* 1989 April; 70(2):113-24]) that inhibits the type of proliferation induced by a BPI protein product and thus includes agents capable of inhibiting the effect or activity of a BPI protein product in enhancing pericyte proliferation, including antibodies that specifically bind to a BPI protein product or a pericyte receptor that recognizes a BPI protein product (including polyclonal antibodies, monoclonal antibodies, fragments thereof, chimeric antibodies, single chain antibodies, humanized antibodies, and human antibodies), antisense polynucleotides (which may bind e.g. to RNA or to DNA in triple helix formation), and compounds (including small molecules) that inhibit the proliferation-promoting activity of BPI by inhibiting the activity of a receptor on pericytes that recognizes BPI protein products, e.g. by inhibiting binding to, interaction with, or signal transduction of the receptor. The activity of a receptor can be inhibited by, e.g., antibodies that specifically bind to the receptor, antisense polynucleotides that inhibit expression of the receptor, molecules or peptides that competitively inhibit binding of BPI protein products to the receptor, or molecules that antagonize the receptor.

The invention also provides methods of screening for other BPI protein products that enhance pericyte proliferation. Such methods would comprise steps of, e.g., contacting pericytes with a BPI protein product and measuring growth or proliferation of the cells. Optionally the screening methods involve a further step of testing selected candidate compounds in in vitro models or animal models of pericyte proliferation known in the art wherein the proliferation results in desirable effects. Animal models are not well defined for pericyte growth. Studies performed to date quantitate pericyte levels in young versus old animals but not in adult animals (vis a vis changes in pericyte levels). In vitro studies are usually conducted with pericyte co-culture models. Usually pericytes are cultured along with endothelial cells or smooth muscle cells or are isolated and maintained as primary cultures from lung, brain, retina or other tissue. See, e.g., Khoury et al., 1998, *Microvasc. Res.* 56:71; Verbeek et al., 1997, *J. Neurochem.*, 68:1135; Doherty et al., 1998, *J. Bone and Mineral Res.*, 13:828; Nehls et al., 1994, *Microvasc. Res.* 48: 349-363, D'Amore *Semin Cancer Biol* 3(2):49-56, 1992, D'Amore, 1990, "Culture and Study of Pericytes" in *Cell Culture Techniques in Heart & Vessel Research*, Springer Verlag, N.Y., pages 299-314. The screening methods may also involve a further step of testing selected candidate compounds for ability to inhibit endothelial cell proliferation or angiogenesis in cell culture assays or animal models known in the art, e.g. those described in U.S. Pat. Nos. 5,639,727, 5,807,818 and 5,837,678 and International Publication No. WO 94/20128 (PCT/US94/02401), and in-co-owned, co-pending U.S. Ser. No. 09/602,811 filed Jun. 23, 2000 and corresponding International Publication No. WO 01/00655 (PCT/US00/17358), all of which are incorporated by reference herein. BPI protein products, including BPI-derived peptides, can be screened for proliferation-promoting activity using these methods. In addition, the rational design of molecules that function like pericyte proliferation-enhancing BPI protein products is contemplated. For example, peptides or other organic molecules may be synthesized that mimic the structure and function of BPI protein products with the desired pericyte proliferation-enhancing activity.

Further provided are compounds identified by these screening methods described herein as well as methods of using these compounds for treating conditions associated with, resulting from or exacerbated by pericyte degeneration.

The invention further provides methods of screening organic or inorganic compounds for the ability to inhibit proliferation induced by BPI protein products. Suitable standards for use in such screening assays include any BPI protein product that enhances pericyte proliferation, e.g., $rBPI_{21}$ or XMP.679. Such methods would comprise steps of, e.g., contacting pericytes with a BPI protein product and a candidate compound, and measuring growth or proliferation of the cells in the presence and absence of the test compound. Optionally, as a control, the growth or proliferation of the pericytes is also measured in the presence and absence of the test compound alone (in the absence of BPI protein product). The screening methods may involve a further step of testing selected candidate compounds in in vitro models or animal models of pericyte proliferation known in the art wherein the proliferation results in deleterious effects. See, e.g., D'Amore, "Culture and Study of Pericytes" in *Cell Culture Techniques in Heart & Vessel Research*, Springer Verlag, N.Y., pages 299-314 (1990).

Pericyte assays are preferably conducted using primary cultures of bovine retinal pericytes as described in Example 2.

Alternatively, the receptor present on the surface of pericytes can be identified by, e.g., immunoaffinity purification using a BPI protein product and this receptor can be used in an initial screen to identify chemical compounds that bind the receptor.

These methods according to the invention can be used for high throughput screening of libraries of molecules, such as inorganic or organic compounds (including bacterial, fungal, mammalian, insect or plant products, peptides, peptidomimetics and/or organomimetics).

Further provided are compounds identified by these screening methods as well as methods of using these compounds for treating in conditions associated with, resulting from or exacerbated by pericyte proliferation.

Sources for test compounds to be screened include (1) inorganic or organic chemical libraries, (2) natural product libraries, or (3) combinatorial libraries comprised of either random or mimetic peptides, oligonucleotides or organic molecules. Chemical libraries may be readily synthesized or purchased from a number of commercial sources, and may include structural analogs of known compounds or compounds that are identified as "hits" or "leads" via natural product screening. The sources of natural product libraries are collections of microorganisms (including bacteria or fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and/or variants (non-naturally occurring) variants thereof. For a review, see *Science* 282: 63-68 (1998). Combinatorial libraries are composed of large numbers of peptides, oligonucleotides or organic compounds and can be readily prepared by traditional automated synthesis methods, PCR, cloning or proprietary synthetic methods. Of particular interest are peptide or oligonucleotide combinatorial libraries. Still other libraries of interest include peptide, protein, peptidomimetic, multiparallel synthetic collection, recombinatorial, or polypeptide libraries. For a review of combinatorial chemistry and libraries created therefrom, see Myers, *Curr. Opin. Biotechnol.* 8:701-707 (1997). For reviews and examples of peptidomimetic libraries, see Al-Obeidi et al., *Mol. Biotechnol,* 9(3):205-23 (1998); Hruby et al., *Curr Opin Chem Biol,* 1(1):114-19 (1997); Domer et al., *Bioorg Med Chem,* 4(5):709-15 (1996) (alkylated dipeptides). A variety of companies have constructed chemical libraries and provide their use for screening, including for example, 3-Dimensional Pharmaceuticals, Exton, Pa.; Agouron Pharmaceutical, La Jolla, Calif.; Alanex Corp., San Diego, Calif.; Ariad Pharmaceuticals, Cambridge, Mass.; ArQule, Inc., Medford, Mass.; Arris Pharmaceutical, S. San Francisco, Calif.; Axys, S. San Francisco, Calif.; Biocryst Pharmaceuticals, Birmingham, Ala.; Cadus Pharmaceuticals, Tarrytown, N.Y.; Cambridge Combinatorial, Cambridge, UK; ChemGenics, Cambridge, Mass.; CombiChem, San Diego, Calif.; Corvas International, San Diego, Calif.; Cubist Pharmaceuticals, Cambridge, Mass.; Darwin Molecular, Bothell, Wash.; Houghten Pharmaceuticals, San Diego, Calif.; Hybridon, Cambridge, Mass.; Isis Pharmaceuticals, Carlsbad, Calif.; Ixsys, San Diego, Calif.; Molecumetics, Bellevue, Wash.; Peptide Therapeutics, Cambridge, UK; Pharmacopia, Princeton, N.J.; SUGEN, Redwood City, Calif.; Telik, Inc., S. San Francisco, Calif.; or Tripos, Inc., St. Louis, Mo.

Example 1 describes the effect of BPI protein products on bovine retinal endothelial cells. Example 2 describes the effect of BPI protein products on primary cell cultures of bovine retinal pericytes and on a cell line of human retinal pericytes, as well as on MAP kinase phosphorylation. Example 3 describes the effect of BPI protein products on bovine retinal pigment epithelial cells. Example 4 describes studies with BPI protein products in a variety of animal models, including a neonatal mouse model of retinal neovascularization.

EXAMPLE 1

Effect on Bovine Retinal Capillarm Endothelial Cells

Primary cultures of bovine retinal endothelial cells (BREC) were isolated by homogenization and a series of filtration steps as described in King et al., *J. Clin. Invest.,* 1985, 75:1028-36. BREC were subsequently cultured with endothelial cell basal medium (EBM; Clonetics, San Diego, Calif.). supplemented with 10% plasma-derived horse serum (PDHS), 50 mg/l heparin, and 50 µg/ml endothelial cell growth factor (ECGF, Roche, Indianapolis, Ind.). Cells were characterized for homogeneity by their immunoreactivity with anti-factor VIII antibody. Cells remained morphologically unchanged under these conditions, as confirmed by light microscopy. Only cells from passages 2 through 7 were used for the experiments.

A cell growth assay was performed as follows: Cells were plated onto 12-well culture plates and incubated overnight. The cells were treated with vehicle, vascular endothelial growth factor (VEGF, R & D Systems, Minneapolis, Minn.) at 25 ng/ml, serum, compounds, or combinations thereof. The medium is changed during the incubation period, with fresh medium and fresh test compound added every 2 days. After incubation for indicated time period at 37° C., the cells were lysed in 0.1% SDS and DNA content was measured by means of Hoechst-33258 dye and a fluorometer (model TKO-100, Hoefer Scientific Instruments, San Francisco, Calif.). It has been shown that total cellular DNA content measured in this manner correlates closely with actual cell number as determined by hemocytometer counting of trypsinized cells.

Determinations were performed in triplicate and all experiments were repeated at least three times. Results are expressed as the mean ±standard deviation, unless otherwise indicated. Statistical analysis employed Student's t-test or analysis of variance to compare quantitative data populations with normal distributions and equal variance. Data were analyzed using the Mann-Whitney rank sum test or the Kruskal-Wallis test for populations with non-normal distributions or unequal variance. A P-value of <0.05 was considered statistically significant.

No differences were observed in growth between vehicle treated and non-treated cells with regard to total DNA content. $rBPI_{21}$ alone (without addition of VEGF) at 25 or 75 μg/ml also did not have a significant effect. However, the addition of VEGF at 25 ng/ml increased significantly the amount of DNA content by 3 to 5 fold ($p<0.01$). The addition of VEGF and either vehicle or 25 μg/ml of $rBPI_{21}$ did not have a significant effect. In contrast, the addition of VEGF and 75 μg/ml of $rBPI_{21}$ decreased significantly the DNA content ($p<0.05$), indicating that $rBPI_{21}$ was able to inhibit VEGF-dependent growth of bovine retinal capillary endothelial (BREC) cells at a concentration of 75 μg/ml.

Results showed that XMP.679 appears to have a slight growth inhibitory effect itself against BREC at 15 μg/ml, although this effect was not statistically significant. Again, the addition of VEGF alone at 25 ng/ml increased DNA content by 3 to 4 fold. The addition of VEGF and XMP.679 at 1 μg/ml had no effect, but the addition of VEGF and XMP.679 at 5 and 15 μg/ml totally prevented VEGF-dependent growth of BREC.

In additional experiments, cell growth assays as described above were conducted with 25 or 75 μg/ml $rBPI_{21}$ or 5 or 15 μg/ml XMP.679 (with and without addition of 25 ng/ml VEGF) and similar results were observed. The addition of VEGF and 25 μg/ml $rBPI_{21}$ again did not have a significant effect on DNA content. However, the addition of VEGF and 75 μg/ml $rBPI_{21}$ again prevented VEGF-dependent growth of BREC. Likewise the addition of VEGF and 5 or 15 μg/ml XMP.679 again prevented VEGF-dependent growth of BREC. Experiments with lower concentrations of BPI protein products (5 μg/ml $rBPI_{21}$ or 1 μg/ml XMP.679), with and without the addition of VEGF, did not have a significant effect on DNA content. These experiments demonstrate that exemplary protein products $rBPI_{21}$ or XMP.679 inhibit VEGF-dependent growth of bovine retinal capillary endothelial cells.

EXAMPLE 2

A. Effect on Bovine Retinal Pericyte Cells

Primary cultures of bovine retinal pericytes (BRPC) were isolated by homogenization and a series of filtration steps as described in King et al., *J. Clin. Invest.*, 1985, 75:1028-36. BRPC were cultured in Dulbecco's modified Eagle's medium (DMEM, Gibco BRL, Grand Island, N.Y.) with 5.5 mM glucose and 20% fetal bovine serum (FBS, Gibco BRL, Grand Island, N.Y.). Cells were characterized for homogeneity by their immunoreactivity with monoclonal antibody 3G5 [Nayak et al., *J. Exp. Med.* 1988, 167:1003-15]. Cells remained morphologically unchanged under these conditions, as confirmed by light microscopy. Only cells from passages 2 through 7 were used for the experiments.

A cell growth assay was performed as described above in Example 1 and the medium was changed, with fresh medium and fresh test compound added every 2 or 3 days, preferably every 2 days. At 5% FBS, DNA content did not change after six days. At 20% FBS a six to seven fold increase of total DNA was detected.

Figure 1B:
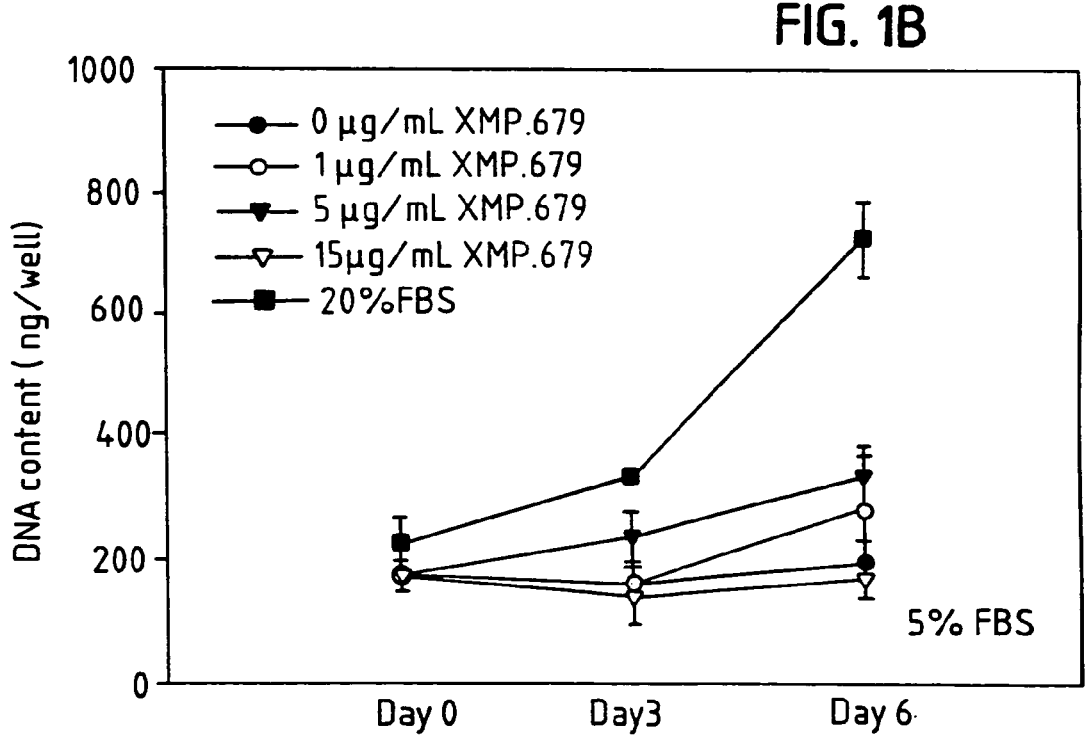

The addition of $rBPI_{21}$ at 5, 25, 75 μg/ml in the presence of 5% FBS increased DNA content in a dose responsive manner. At 75 μg/ml, a 5 fold increase of DNA above basal level was noted. XMP.679 at 1or 5 μg/ml increased growth at 6 days, whereas 15 μg/ml of XMP.679 did not increase growth of the pericytes at either 3 or 6 days above basal which was similar to the effect of 5% FBS. Results are depicted in FIGS. 1A ($rBPI_{21}$) and 1B (XMP.679).

These results indicate that $rBPI_{21}$ enhanced growth of retinal pericytes in a dose responsive manner with a maximum observed at 75 μg/ml that almost equaled the growth effect of 20% FBS. XMP.679 was able to increase growth at 5 μg/ml, which reached about 30 to 40% the potency of 20% FBS. At a higher concentration, XMP.679 did not show-a growth stimulating effect.

The experiment was repeated in combination with 10% FBS. Again, similar findings were observed. Addition of $rBPI_{21}$ induced the growth of pericyte at 10% FBS at concentrations of 5, 25 and 75 μg/ml. Interestingly, 25 and 75 μg/ml of $rBPI_{21}$ appeared to improve growth above that of 20% FBS. XMP.679 at 5 μg/ml equaled the effect of 20% FBS, whereas 15 μg/ml did not have much growth effect. These results indicated that, at 10% FBS, $rBPI_{21}$ may have more growth effect than 20% FBS. This is quite unusual, since not many growth factors can improve the growth effects of 20% FBS in enhancing the growth of retinal pericytes.

The experiment was repeated with 15% FBS, which can stimulate pericyte growth by approximately 6-8 fold after six days of incubation. Again, 20% FBS was more potent as well as reaching a higher level of growth after 6 days then 15%. The addition of 75 μg/ml $rBPI_{21}$ increased the growth greater then 20% FBS. In comparison, the addition of XMP.679 did not increase the growth of pericyte in 15% FBS to any significant amount. These results indicated that even at 15% FBS, $rBPI_{21}$ was able to stimulate more growth then either 15 or 20% FBS. The effect of XMP.679 was less than that of $rBPI_{21}$. There is a trend that, at 5 μg/ml of XMP.679, it may have more growth effect than either 15 or 20% FBS.

The conclusion from these data is that $rBPI_2$, and, to a lesser extent, XMP.679, enhanced proliferation of retinal pericytes. This enhanced growth was dose-dependent, with $rBPI_{21}$ at 75 μg/mL resulting in a 3-fold stimulation (there was no net growth in the controls). XMP.679 showed perhaps a 2-fold stimulation at 5 μg/mL, but no enhancement at 15 μg/mL. This observation was reproducible and occurred in 5, 10 or 15% FBS.

In additional experiments, both the DNA content and total cell number per well were determined in BRPC treated with 5, 25, 75 μg/ml $rBPI_{21}$ in the presence of 5% FBS. The addition of $rBPI_{21}$ at 5, 25, 75 μg/ml in the presence of 5% FBS again increased DNA content in a dose responsive manner. Similarly, the total number of cells per well also increased in a dose responsive manner. These observations indicate that the $rBPI_{21}$ induced dose dependent increase in DNA content correlates with the rBPI$_{21}$ induced dose dependent increase in proliferation of bovine retinal pericytes.

Growth assays were also repeated with 1, 5, 15 μg/ml XMP.679 and with additional concentrations of 10 or 20 μg/ml XMP.679 at 10% FBS. Statistically significant increases in pericyte DNA content were measured at 1, 5, 10, and 15 μg/ml XMP.679. Similar results as above were observed with 5 μg/ml XMP.679 again showing the greatest increase in retinal pericyte proliferation, while a higher concentration of XMP.679 (20 μg/ml) did not.

Experiments were also performed in which the level of MAP kinase phosphorylation was determined in BRPC treated with 75 μg/ml rBPI$_{21}$ or 5 μg/ml XMP.679. The level of MAP kiriase phosphorylation was determined 1, 3, 5, 15, 30 and 60 minutes after the addition of rBPI$_{21}$ or XMP.679. rBPI$_{21}$ increased MAP kinase phosphorylation over time with a maximum phosphorylation 15 minutes after the addition of rBPI$_{21}$ that nearly equaled the effect of 20% FBS. XMP.679 increased MAP kinase phosphorylation over time with a maximum phosphorylation between 15 and 60 minutes. These observations indicate that exemplary BPI protein products rBPI$_{21}$ and, to a lesser extent, XMP.679, enhance MAP kinase phosphorylation in BRPC. Moreover, these results suggest that the BRPC MAP kinase phosphorylation is useful for the screening of other compounds for this stimulatory activity.

B. Effect on Human Retinal Pericyte Cells

In addition to studies with primary cell cultures of bovine retinal pericytes described above, experiments were performed with a human cell line obtained from Clonetics (San Diego, Calif.) of retinal pericytes (catalog no. CC-2542 PyCRt). These human retinal pericytes (HRPC) were cultured in Dulbecco's modified Eagle's medium (DMEM, Gibco BRL, Grand Island, N.Y.) with 5.6 mM glucose and 20% fetal bovine serum (FBS, Gibco BRL, Grand Island, N.Y.).

Proliferation assays were performed as follows: HRPC were plated onto 24-well culture plates (3000 cells/well) in 5 or 10% FBS-DMEM with 5.6 mM glucose and incubated overnight. The cells were treated once with vehicle alone or with vehicle and several concentrations of XMP.627 ([SEQ ID NO: 4]), XMP.664 ([SEQ ID NO: 5]), XMP.679 ([SEQ ID NO: 3]), or XMP.728 ([SEQ ID NO: 6]) for 5 or 6 days. The medium was not changed, nor were additional amounts of test compounds added as described in the experiments of part A above. The cells were fixed and stained with Methylene blue and proliferation assayed by observation at OD$_{650}$.

The addition of XMP.679 at approximately 0.5, 1, 5, 8 μg/ml in the presence of 5% FBS increased HRPC proliferation in a dose responsive manner, with a maximum observed at approximately 5 μg/ml. Results showed that XMP.679 at concentrations of 10 μg/ml and higher appeared to have a slight growth inhibitory effect itself against HRPC. When the experiment was repeated in the presence of 10% FBS, similar findings were observed.

The addition of XMP.664 at approximately 0.5, 1, 5 μg/ml similarly increased HRPC proliferation in a dose responsive manner in the presence of 5% FBS, with a maximum observed at approximately 5 μg/ml. Results showed that XMP.664 at concentrations of 10 μg/ml and above XMP.664 appears to have a slight growth inhibitory effect against HRPC. When the experiment was repeated in the presence of 10% FBS, results showed 10 μg/ml XMP.664 increased HRPC proliferation, while XMP.664 above 10 μg/ml inhibited proliferation.

The addition of XMP.627 at approximately 0.5, 1, 5, 8 μg/ml in the presence of 5% FBS increased HRPC proliferation in a dose responsive manner, with a maximum observed at approximately 5 μg/ml. XMP.627 appears to have a slight growth inhibitory effect itself against HRPC above 10 μg/ml. The addition of XMP.627 in the presence of 10% FBS did increase HRPC proliferation.

The addition of XMP.728 similarly increased HRPC proliferation at only at approximately 5 μg/ml in the presence of 5% FBS, and to lesser extent in the presence of 10% FBS.

These results indicate that XMP.679 enhanced proliferation of HRPC with a maximum observed at approximately 5 μg/ml. Similarly, additional exemplary BPI protein products XMP.627, XMP.664, and XMP.728 showed similar HRPC stimulatory activity.

In an initial experiment with rBPI$_{21}$, with HRPC, and in contrast to the results with primary cell cultures of bovine retinal pericytes described in part A above, little or no proliferation was observed. Similar results were obtained in an initial experiment with rBPI$_{50}$, rBPI$_{42}$, and fusion proteins such as a BPI-Ig fusion (e.g., rBPI$_{23}$-Ig) or a BPI-LBP fusion (e.g. P4161 as described in Abrahamson et al., Journal of Biological Chemistry, 272: 2149-2155 (1997),) as well as XMP.711 ([SEQ ID NO: 7]), XMP.852 ([SEQ ID NO: 8]), and XMP.861 ([SEQ ID NO: 9]). XMP.718 ([SEQ ID NO: 10]) and XMP.365 ([SEQ ID NO: 11]) appeared to exhibit some toxicities on HRPC in an initial assay. In contrast, XMP.629 ([SEQ ID NO: 12]), XMP.676 ([SEQ ID NO: 13]), XMP.768 ([SEQ ID NO: 14]), and XMP.851 ([SEQ ID NO: 15]), enhanced the proliferation of HRPC. Additional assays are conducted with BPI protein products, wherein the cell culture medium is changed and additional amounts of test compound is added as described in the experiments of part A above, and the enhancement of proliferation of HRPC is measured as described above.

EXAMPLE 3

Effect on Bovine Retinal Pigment Epithelial Cells

Bovine retinal pigment epithelial cells (RPEC) were isolated by gentle scraping after removal of the neural retina and incubation with 0.2% collagenase as described in King et al., *Diabetes,* 1987, 36:1460-7. RPEC were cultured in DMEM with 5.5 mM glucose and 10% calf serum (CS, Gibco BRL, Grand Island, N.Y.). Cells were cultured in 5% CO$_2$ at 37° C., and media were changed every other days. Cells were characterized for their homogeneity by immunoreactivity with anti-cytokeratin antibody for RPEC. Cells remained morphologically unchanged under these conditions, as confirmed by light microscopy. Only cells from passages 2 through 7 were used for the experiments.

Figure 2:
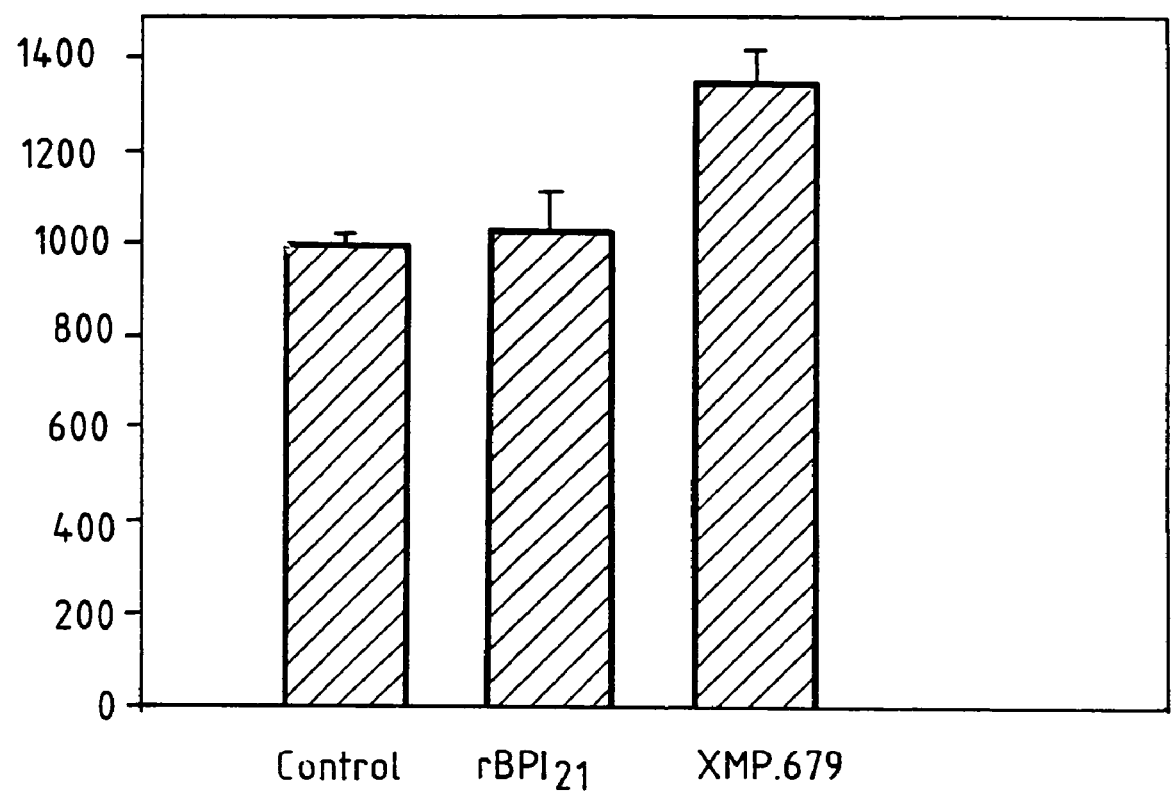
FIG. 2 displays effects of BPI protein products on bovine retinal epithelial cell proliferation.

A cell growth assay was performed as described above in Example 1. Results are shown in FIG. 2. The addition of rBPI$_{21}$ had no effect at 75 μg/ml. XMP.679 had some (approximately 20 to 30%) growth promoting effect at 15 μg/ml.

EXAMPLE 4

In Vivo Effects of BPI Protein Products

A. In Vivo Assay for Anti-Angiogenesis Effect in Neonatal Mice

To produce ischemia-induced retinal neovascularization, litters of 7-day-old (postnatal day 7, P7) C57BL/6J mice and their nursing mothers were exposed to 75±2% oxygen for 5 days and then returned to ambient air at age P12 as described in Smith et al., *Invest. Ophthalmol. Vis. Sci.*, 1994, 35:101-111. Intraperitoneal injections of XMP.679 (10 mg/kg) were performed every 24 hrs from P12 to P17. Control animals received saline. After sacrifice and enucleation, flat-mounted, fluorescein-conjugated dextran-perfused retinas were examined to assess the retinal vasculature.

This mouse model reflects the effects of hypoxia on inducing angiogenesis in the retina. After birth, the mice are exposed to a high level oxygen for 4-5 days. The effect of high levels of oxygen will decrease or prevent the growth of blood vessels in the retina. Once the mice have been removed from the hyperoxic condition to normal oxygen levels, the retina will develop hypoxia due to the lack of blood vessels. The hypoxia in the retina will induce many growth factors (including VEGF) which leads to a angiogenic response that can be quantitated by measuring the number of nuclei in the blood vessels above the internal limiting membrane. This mouse model of angiogenesis is thought to be a good animal reflection of retinopathy of prematurity. The main growth factor responsible for retinal angiogenesis in this mouse model is thought to be due to the expression of VEGF.

As in previous studies, examination of the flat-mounted, fluorescein-conjugated dextran-perfused retinas and hematoxylin-eosin stained sections of tissue obtained after 5 days of hypoxia from control animals showed neovascular rufts, particularly in the mid-periphery, extending above the internal limiting membrane into the vitreous. These neovascular rufts were most prominent on P17-19, but after P23 the neovascularization regressed, and the vascular pattern normalized by P26.

As described in Aiello et al., *Proc. Nat'l Acad. Sci. USA*, 1995, 92:10457-61, mice at P17 (n=5) were deeply anesthetized with pentobarbitol sodium (100 mg/kg) and sacrificed by cardiac perfusion with 4% paraformaldehyde in phosphate-buffered saline. Eyes were enucleated and fixed in 4% paraformaldehyde at 4° C. overnight, and enbedded in paraffin. Over 50 serial sections (6 µm) including optic nerve head were placed on microscope slides. After staining with periodic acid/Schiff reagent and hematoxylin, 10 intact sections of equal length, each 30 µm apart, were evaluated for a span of 300 µm. All retinal vascular cell nuclei anterior to the internal limiting membrane were counted in each section by a fully masked protocol. The mean of all 10 counted sections yielded average neovascular cell nuclei per 6 µm section per eye. No vascular cell nuclei anterior to the internal limiting membrane are observed in normal unmanipulated animals.

The retina of mice given XMP.679 via daily intraperitoneal injections showed fewer blood vessels with much less density and tortuosity then those observed in control mice. XMP.679 also reduced the number of nuclei above the internal limiting membrane and decreased the number of nuclei anterior to the internal limiting membrane (p<0.001) by approximately 30 to 40%.

In addition to the experiments with 10 mg/kg XMP.679 as described above, experiments with 20 mg/kg XMP.679 were performed. Similar findings were observed. The retina of mice (n=6) given 20 mg/kg XMP.679 via daily intraperitoneal injections showed reduced number of nuclei above the internal limiting membrane and decreased the number of nuclei anterior to the internal limiting membrane (p<0.01) by approximately 71%. These results indicate that an exemplary BPI protein product XMP.679 inhibits retinal neovascularization in a dose responsive manner (e.g., in the range of 10-20 mg/kg) in neonatal mice.

B. In Vivo Assay for Anti-Angiogenesis Effect In Rats

In contrast to the assay for anti-angiogenesis effect of BPI protein products in neonatal mice described in part A above, experiments were conducted in newborn rats Crj:CD(SD) IGS (Charles River, Japan). Unlike the method described in part A above of producing ischemia-induced retinal neovascularization by exposing neonatal mice to a constant level of oxygen at 75±2% for 5 days, newborn rats were exposed to oxygen pulses as described below.

The newborn rats within a few hours after birth were put into the oxygen chamber (780 mm×520 mm×520 mm). The oxygen level in the experimental chamber was controlled with a computer program (Oxycycler, Reming Bioinstruments, N.Y., US). The oxygen level was maintained at 80% for 20.5 hours, then rapidly dropped to 21% for 30 minutes before a gradual return to 80% during the following 3 hours. The program was run for 11 cycles (24 hour per cycle). At the end of $11^{th}$ cycle (postnatal day 11 (P11)), mothers and newborn rats were transferred to room air condition and kept for 7 days. For a seven day period step newborn rats were injected intraperitoneally with XMP.679 at doses of 2, 6 and 20 mg/kg. On P18, the rats were sacrificed, and the left eyes were enucleated. The eyes were fixed in 4% paraformaldehyde (PFA) for 1 hour. Using scissors, the cornea and sclera were removed from the eyecup. The lens was removed with tweezers, and the vitreous was thoroughly removed with tweezers and scissors. The semi-spherical retina was fixed in 4% PFA and stained, using the method of adenosine diphosphatase (ADPase) histochemistry. Abnormal neovascularization was assessed on P18 by histochemically staining retina for ADPase activity. This procedure preferentially stains retinal vascular endothelium and microglia in rats of this age. The retina was incubated in ADPase incubation medium at 37° C. for 1 hour with gentle agitation. It was then washed thoroughly in cold saline, and treated in a 1:10 dilution of ammonium sulfide for 1 minute. The retina was then washed in silane to remove sulfide. The retina was placed in a small drop of liquid on a saline-coated slide. Release the curve of the retina with 4 radial cut to define superior, inferior, nasal and temporal quadrants. The retina was put in a layer of Perma Fluor® covered with a cover glass. Glomerular buds (tiny popcorn) upon the surface of the regina, fan shaped neovascular fronds, and ridges (vascular complexes that cause a distinct elongate elevation of the retinal surface, and which usually contain several vessels running parallel to the ciliary body) were identified.

Criteria for scoring neovascular intensity were as follows: 0: Nothing; 1: <5 buds; 2: >5 buds, or a frond; 3: Ridge<half of quadrant; or 4: Ridge>half of quadrant. The retinal neovascular scores were equal to the sum of quadrant scores. These scores were 6.41 in vehicle-injected eyes, and 7.29, 4.59 and 5.56 in the eyes of XMP.679 injected rats (2, 6 and 20 mg/kg/day, respectively). Although the differences were not statistically significant, the retinal neovascularization score was reduced by XMP.679 at 6 mg/kg.

C. In Vivo Studies in Hypergalactosemic Rats

Additional in vivo studies are carried out with test compounds, including BPI protein products, either in hypergalactosemic rats [Kem and Engermann, 1995, *Arch. Ophthalmol.*, 114(8):986-990] or in transgenic mice overexpressing PKC β isoform in the blood vessels with the induction of diabetes by STZ [Robison et-al., *Curr. Exp. Res.* 10:338

(1991)]. [Ruggiero et al., 1997 *Diabetes & Metabolism* 23:30-42; Hirschi & D'Amore, *Cardiovasc Res* 1996 October;32(4):687-98.]

D. Studies of Choroidal Neovascularization Membrane Formation in Laser Treated Rats.

The effect of test compounds, including BPI protein products, in an age-related model of macular degeneration are also studied in a primate model [Monaco & Wormington *Optom Vis Sci* 1990 July;67(7):532-7; Hope et al., *Br J Ophthalmol*. 1992 January;76(1): 11-6]. Additionally, to demonstrate the use of test compounds, including BPI protein products, as a therapy for the wet form of age related-macular degeneration, their effects on choroidal neovascular membrane (CNVM) formation in laser treated rats are studied. Assays are performed as follows.

Adult male Brown Norway rats (Harlan Sprague Dawley, Inc., Indianapolis, Ind.) are anesthetized (75 mg/kg ketamine, 2.5 mg/kg acepromazine, and 0.05 mg/kg atropine to minimize bronchial secretions) and undergo pupillary dilation (topical cyclopentolate 1%, phenylephrine 2.5%, and atropine sulfate 1%). The animals are positioned on a Mayo stand and the fundus is visualized using a microscope slide cover slip and goniosol as a contact lens. Eight Krypton red photocoagulation burns (150 mW, 199 uM, 00.5 sec) are applied in the funds at equal distances surrounding the optic disk. This intensity produced ruptures in Bruch's membrane with reproducible CNVM formation and minimal collateral damage to the mid and inner retina. Providone 5% is applied to the ocular surface, and a topical anesthesia ( 0.5% propoparacaine hydrochloride) is applied prior to an intravitreal injection. Immediately (within ~5 minutes) after placement of the laser photocoagulation burns, animals receive a single intravitreal injection of a test compound, including a BPI protein product, in one eye, and the control vehicle is injected into the contralateral eye. Groups of animals receive different dosage of test compound, such as a BPI protein product—for example, by intraperitoneal or intravitreal administration. Another group receives no intravitreal injections and serve as laser-only controls.

At 14 days post-treatment one half of the animals from each dosage group undergo fundus photography, fluorescein angiography, and histopathology of retrieved eyes, to assess neovascularization. At 28 days post-treatment the remaining animals from each dosage group, as well as laser-only controls, undergo neovascularization assessment.

Fundus color photography is used determine the size of the laser burn, as well as the presence of subretinal vessels, subretinal hemorrhage, and subretinal fluid. CNVM are graded on a fluorescein angiogram classification scheme [Reinke et al, Invest. *Ophthalmology Vis Sci (Suppl)* 1996; 37, 125] Fluorescein angiogram findings are correlated with those from histopathology. For histophathogy, the eyes are enucleated and eyecup preparations fixed overnight at room temperature with in 4% phosphate-buffered paraformaldehyde. Tissue sections are dehydrated, embedded in paraffin, 6 um sectioned are stained with hematoxylin and eosin for light microscopy. Histologic specimens are examined by light microscopy for presence or absence of neovascularization; the level of neovascularization with respect to the choroid, Bruch's membrane, or the retina; the response or the RPE cells to original injury and subsequent CNVM. Additionally, ocular toxicology of test compounds, including BPI protein products, on the eye is clinically evaluated and graded, and the tissue and cellular characteristics are evaluated histopathologically.

E. In Vivo Anti-Permeability Studies

1.) Effects on VEGF-Induced Retinal Vascular Permeability

The effects of a test compound, including a BPI protein product, on VEGF-induced vascular permeability in an in vivo rat model is determined by vitreous flourophotometry as described in Aiello et al., *Diabetes* 1997; 40:1473-1480. Assays are performed as follows.

Adult male Sprague-Dawley rats are treated, for example, by intravitreal or intraperitoneal administration of test compounds, such as BPI protein products, or vehicle alone. A catheter is implanted into the right jugular vein 24 hrs prior to vitreous flourophotometry. Baseline vitreous fluorescence measurements are obtained from all animals to correct for intrinsic fluorescence and subtracted from all subsequent vitreous fluorescence measurements. VEGF (2 ng eye, 25ng/ml final) is injected intraocularly at time 0 into one eye and bovine serum albumin (BSA)isaline control is administered to contralateral eye. Fifteen minutes later, 30-65 µl of 10% sodium fluorescein is (Akom, Abita Springs, Calif.) is injected into through the jugular catheter. Vitreous fluorescein leakage is measured by fluorphotomotry 40 minutes after baseline vitreous fluorescence measurements are made. The accumulation of fluorescein dye in the vitreous of the eye is measured by utilizing the fluorescein excitation wavelength of 488 nm and integrating the resulting fluorescence centered at the fluorescence peak (520 nm) from the center of the vitreous.

2.) Effects on Diabetes-Induced Retinal Vascular Permeability

The effect of test compounds, including BPI protein products, on diabetes induced-retinal vascular permeability is studied in rats as determined by Evans-Blue diffusion as described in Xu et al., *Invest. Opthalmol Vis. Sci.* 2001;42: 789-794. Evans-Blue dye binds to plasma albumin and diffuses into the surrounding tissue over a fixed period of time. The concentration of dye is measured by extracting it from the target tissue and quantifying it by spectrophotometry. The amount of albumin-bound dye in retinal tissue correlates with retinal vascular permeability. Assays are performed as follows.

Sprague-Dawley rats are made diabetic using Streptozotocin and diabetic confirmed by blood glucose measurements after 24 hours. Animals are treated for example, with intraperitoneal or intravitreal administration of test compounds such as BPI protein products or vehicle alone. A polyvinyl catheter (Braintree Scientific, Braintree, Mass.) is implanted into the right jugular vein of anesthetized rats 24 hrs prior to measurements of Evans-Blue dye. On the day of the experiment, Evans-Blue dye (45 mg/kg) is injected into the jugular catheter. Two hours after the dye injection, additional anesthesia is given and a laparotomy is performed to expose the descending vena cava. Heparinized venous blood (0.9 cc) is withdrawn to determine the average plasma dye concentration. The chest cavity is exposed and a 25-gauge butterfly catheter is inserted into the left ventricle. The arch of the vena cava is cut and 30 cc of saline is infused into the heart at physiological pressure through the butterfly catheter. After saline infusion, 30 cc of 10% Formalin is infuse to fix the tissues. Following tissue fixation, the eyes are nucleated. The retina from each eye is isolated using a surgical microscope and placed in pre-weighed ependorf tube. The retina samples are incubated in formamide overnight at 72° C. to extract the Evans-Blue dye. Following incubation, the resulting extract is ultra-centrifuged and the supernatent used for spectrophotometric measurements. Absorbance is measured at 620 nm (Evans-Blue maximum) and 720 nm (Evans-Blue minimum).

Numerous modifications and variations of the above-described invention are expected to occur to those of skill in the art. Accordingly, only such limitations as appear in the appended claims should be placed thereon.

What is claimed is:

1. A method of screening a BPI protein product for the ability to enhance proliferation of pericytes comprising the steps of: (a) detecting proliferation of pericytes in the presence and absence of a BPI protein product; and (b) identifying a BPI protein product as a candidate enhancer of pericyte proliferation when proliferation of the pericytes is increased in the presence of the BPI protein product.

2. The method of claim 1 wherein proliferation is determined by measuring the amount of MAP kinase phosphorylation.

* * * * *